United States Patent
Loughlin et al.

(10) Patent No.: US 12,178,824 B2
(45) Date of Patent: Dec. 31, 2024

(54) ORODISPERSIBLE FORMULATIONS

(71) Applicant: Millicent Pharma Limited, Dundalk (IE)

(72) Inventors: Ryan Loughlin, Banbridge (GB); Roger M. Boissonneault, Branford, CT (US)

(73) Assignee: Millicent Pharma Limited, Dundalk (IE)

( * ) Notice: Subject to any disclaimer, the term of this patent is extended or adjusted under 35 U.S.C. 154(b) by 0 days.

(21) Appl. No.: 18/046,553

(22) Filed: Oct. 14, 2022

(65) Prior Publication Data

US 2023/0080934 A1 Mar. 16, 2023

Related U.S. Application Data

(63) Continuation of application No. 17/431,807, filed as application No. PCT/IB2021/055633 on Jun. 24, 2021.

(60) Provisional application No. 63/172,140, filed on Apr. 8, 2021, provisional application No. 63/084,723, filed on Sep. 29, 2020.

(51) Int. Cl.
*A61K 31/567* (2006.01)
*A61K 9/00* (2006.01)
*A61K 9/20* (2006.01)
*A61P 15/18* (2006.01)

(52) U.S. Cl.
CPC .......... *A61K 31/567* (2013.01); *A61K 9/0056* (2013.01); *A61K 9/2018* (2013.01); *A61K 9/2027* (2013.01); *A61K 9/2054* (2013.01); *A61K 9/2059* (2013.01); *A61K 9/2072* (2013.01); *A61P 15/18* (2018.01)

(58) Field of Classification Search
CPC .. A61K 31/567; A61K 9/0056; A61K 9/2018; A61K 9/2027; A61K 9/2054; A61K 9/2059; A61K 9/2072; A61K 9/2077; A61K 31/565; A61K 2300/00; A61P 15/18; A61P 5/30
See application file for complete search history.

(56) References Cited

U.S. PATENT DOCUMENTS

| | | | |
|---|---|---|---|
| 6,497,899 | B2 | 12/2002 | Thombre et al. |
| 7,132,114 | B2 | 11/2006 | Daggy et al. |
| 7,815,937 | B2 | 10/2010 | Mezaache et al. |
| 8,226,980 | B2 | 7/2012 | Ahmed et al. |

(Continued)

FOREIGN PATENT DOCUMENTS

| | | |
|---|---|---|
| CN | 102058604 A | 5/2011 |
| CN | 102885798 A | 1/2013 |

(Continued)

OTHER PUBLICATIONS

Ghandi (A new adventure in Modern Formulation Technology, The Phama Innovation, vol. 1, No. 8). (Year: 2012).*

(Continued)

*Primary Examiner* — Benjamin J Packard
*Assistant Examiner* — Lucy M Tien
(74) *Attorney, Agent, or Firm* — Venable LLP

(57) ABSTRACT

An orodispersible formulation for contraception or hormone replacement therapy containing an estrogen and a progestogen that has sufficient hardness, disintegration time and friability.

30 Claims, 14 Drawing Sheets

(56) References Cited

U.S. PATENT DOCUMENTS

| | | |
|---|---|---|
| 8,343,978 B2 | 1/2013 | Dong |
| 8,475,838 B2 | 7/2013 | Davila et al. |
| 8,900,602 B2 | 12/2014 | Fujiwara et al. |
| 8,946,153 B2 | 2/2015 | Gupta et al. |
| 9,192,580 B2 | 11/2015 | Green et al. |
| 9,254,294 B2 | 2/2016 | McCarty |
| 9,446,055 B2 | 9/2016 | Fujiwara et al. |
| 9,526,789 B2 | 12/2016 | Park et al. |
| 9,731,018 B2 | 8/2017 | Ahuja et al. |
| 9,795,616 B2 | 10/2017 | Ahmed et al. |
| 9,987,287 B2 | 6/2018 | Platteeuw et al. |
| 10,086,078 B2 | 10/2018 | Ahuja et al. |
| 2007/0196476 A1 | 8/2007 | Withiam et al. |
| 2007/0196477 A1 | 8/2007 | Withiam et al. |
| 2007/0196494 A1 | 8/2007 | Grenier et al. |
| 2007/0286819 A1 | 12/2007 | DeVries et al. |
| 2008/0113953 A1 | 5/2008 | De Vries et al. |
| 2011/0250272 A1 | 10/2011 | Besse et al. |
| 2011/0293720 A1 | 12/2011 | General et al. |
| 2018/0153801 A1 | 6/2018 | Jaspart et al. |
| 2018/0169022 A1 | 6/2018 | Jaspart et al. |
| 2018/0185271 A1 | 7/2018 | Jaspart et al. |
| 2019/0125759 A1 | 5/2019 | Jaspart et al. |

FOREIGN PATENT DOCUMENTS

| | | |
|---|---|---|
| DE | 102006027796 A1 | 12/2007 |
| EP | 1 471 890 B1 | 9/2006 |
| EP | 3 701 944 A1 | 9/2020 |
| IN | 1531921 A | 9/2004 |
| WO | 95/09608 A1 | 4/1995 |
| WO | 2003/086354 A1 | 10/2003 |
| WO | 2004/100857 A2 | 11/2004 |
| WO | 2006/128907 A2 | 12/2006 |
| WO | 2007/104771 A1 | 9/2007 |
| WO | 2010/146551 A2 | 12/2010 |
| WO | 2011/058336 A2 | 5/2011 |
| WO | 2013/100705 A1 | 7/2013 |
| WO | 2015/144830 A1 | 10/2015 |
| WO | 2016/203044 A1 | 12/2016 |
| WO | 2018/130603 A1 | 7/2018 |

OTHER PUBLICATIONS

Etman (Formulation of Desloratadine Oral Disintegrating Tablets, Journal of Applied Pharmaceutical Science vol. 4 (11), pp. 054-061, Nov. 2014.*

H. Omidian, et al., "Swelling agents and devices in oral drug delivery", J. Drug Del. Sci. Tech., 18(2), pp. 83-93 (2008).

G. Sharma, et al., "Mouth dissolving tablets: A current review of scientific literature", Int. J. Pharm. Med. Res., 1(2), pp. 73-84 (2013).

International Search Report and Written Opinion in International Application No. PCT/IB2021/055633 (Sep. 2021).

Liesbeth Meeus, "Direct Compression Versus Granulation," 23(3) Pharmaceutical Technology Europe, 2 pages (Mar. 2011) (https://www.pharmtech.com/view/direct-compression-versus-granulation).

* cited by examiner

ORODISPERSIBLE FORMULATIONS

CROSS REFERENCE TO RELATED APPLICATIONS

This application is a continuation of U.S. application Ser. No. 17/431,807, which was the National Stage of International Application No. PCT/IB2021/055633, filed Jun. 24, 2021, which claims the benefit of U.S. Provisional Application No. 63/084,723, filed Sep. 29, 2020, and U.S. Provisional Application No. 63/172,140, filed Apr. 8, 2021. The entirety of each of these prior applications is incorporated by reference herein.

FIELD OF THE INVENTION

This invention is related to orodispersible solid dosage form and method of making and administering the same.

BACKGROUND OF THE INVENTION

Contraceptive compositions containing both estrogenic and progestogenic compounds are known to be highly effective in controlling ovulation. Such compounds may also be used for hormone replacement therapy to treat symptoms associated with menopause.

There remains a need for a method to increase the bioavailability of hormones administered in solid dosage form thereby increasing their treatment value. When the bioavailability of hormones is increased, the effective dose required can be reduced. Reduced dosing of hormones, especially estrogens, can help to minimize unwanted side effects. There also remains a need to be able to provide a dosage form that is convenient and fast so that patients adhere to the prescribed contraception or hormone replacement regimen without skipping doses.

SUMMARY OF THE INVENTION

The invention is related to an orodispersible solid dosage form, comprising: a first active ingredient in amount up to about 0.5% w/w of the dosage form; an intragranular component; and an extragranular component, wherein the intragranular component comprises: at least one intragranular diluent; at least one intragranular disintegrant; and at least one intragranular binder, wherein the extragranular component comprises: at least one extragranular diluent; and at least one extragranular disintegrant, wherein the intragranular component constitutes from about 40% w/w to about 80% w/w of the orodispersible solid dosage form, wherein an intragranular diluent content is from about 80% w/w to about 97% w/w of the intragranular component, wherein an intragranular disintegrant content is from about 2% w/w to about 5% w/w of the intragranular component, wherein an intragranular binder content is from about 0.2% w/w to about 7% w/w of the intragranular component, wherein an extragranular diluent content is from about 70% w/w to about 88% w/w of the extragranular component, wherein an extragranular disintegrant content is from about 4% w/w to about 12% w/w of the extragranular component, and wherein the orodispersible solid dosage disintegrates in about 60 seconds or less.

This invention is also related to an orodispersible solid dosage form, comprising: a first active ingredient in amount of up to about 0.5% w/w of the dosage form; at least one diluent, where a diluent content is about 80% w/w to about 95% w/w of the orodispersible solid dosage form; at least one binder, where a binder content is about 2% w/w to about 7% w/w of the orodispersible solid dosage form; and at least one disintegrant, where a disintegrant content is about 2% w/w to about 8% w/w of the orodispersible solid dosage form, wherein the orodispersible solid dosage form has an intragranular component and an extragranular component, wherein the intragranular component constitutes from about 40% w/w to about 80% w/w of the orodispersible solid dosage form, wherein the intragranular component comprises the least one diluent, the at least one disintegrant, and the at least one binder, wherein the extragranular component comprises the at least one diluent and the at least one disintegrant, and orodispersible solid dosage form disintegrates in about 60 seconds or less.

The invention is also directed to an orodispersible solid dosage form comprising: ethinyl estradiol or a prodrug thereof in amount of about 0.001% w/w up to about 0.05% w/w; at least two diluents in an amount of about 80% w/w to about 95% w/w, wherein the diluents comprise mannitol and microcrystalline cellulose; at least one binder in an amount of about 2% w/w to about 7% w/w, wherein the at least one binder comprises a pregelatinized starch and/or povidone; and at least one disintegrant in an amount of about 2% w/w to about 8% w/w, and wherein the orodispersible solid dosage disintegrates in about 60 seconds or less.

DETAILED DESCRIPTION OF THE INVENTION

Figure 1:
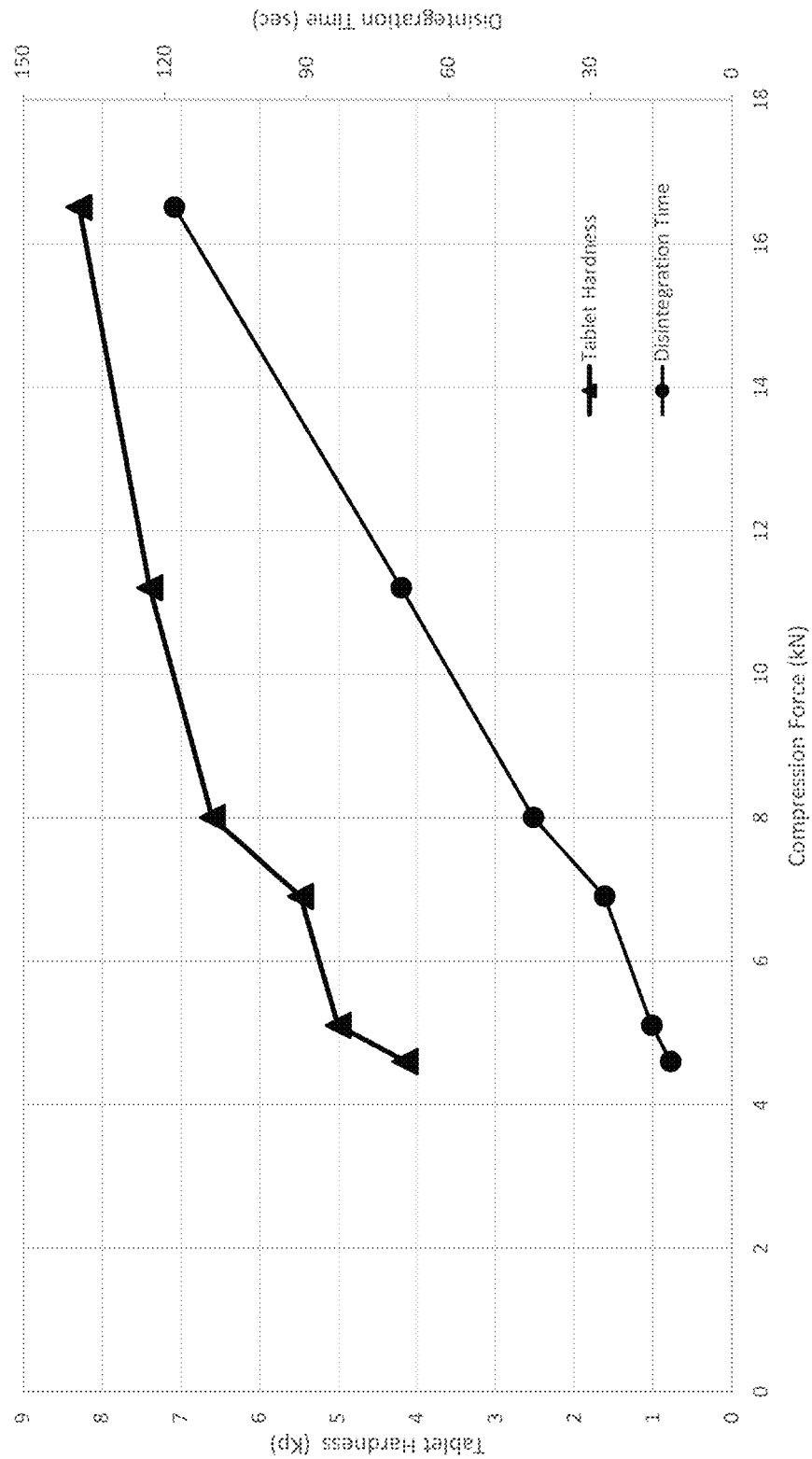
FIG. 1 is a graph depicting the compression force, hardness and disintegration time of an orodispersible solid dosage form of Example 1.

Conventional oral contraceptives and/or hormone replacement therapy using estrogen are formulated as pills or tablets intended to be swallowed. Oral contraceptives and/or hormone replacement therapy can be in a form of chewable tablets as well, but such tablets must be chewed and at least some portion thereof can then also end up being swallowed. While there are non-oral contraceptives and/or hormone replacement therapies, such as intravaginal devices (e.g., vaginal rings) or intrauterine devices (e.g., IUDs), intended to improve adherence to the contraceptive and/or hormone replacement regimens, some patients still prefer oral administration. For instance, there is a need for an alternative estrogen-containing oral contraceptive and/or hormone replacement therapy, which can make it easier to adhere to the prescribed regimen, especially for patients who have difficulty swallowing pills.

Estrogen exposure is also a consideration, especially in connection with contraceptive regimens, which may necessitate higher amounts to be administered to provide a desired level of effectiveness. However, higher or elevated levels of estrogen are associated with undesirable side effect, for example, bloating, gastro-intestinal upsets, swelling, weight gain, fatigue, mood swings and vaginal dryness and vaginal atrophy. Transdermal estrogen patches provide an alternative that some users believe to possess less risk of serious estrogen related side effects. While it is well known that transdermal delivery of hormones can minimize gastrointestinal upset and avoid first pass and first pass metabolism associated with oral dosing, patches are not as easy to use as oral contraceptives and they can potentially detach.

Bioavailability of an estrogen may be improved when it is absorbed buccally, sublingually, or sublabially, whereby at least a portion of the administered the estrogen avoids the digestive tract. Oral absorption allows estrogen to directly enter the bloodstream avoiding hepatic first pass and first pass metabolism. It is believed that since hepatic first pass and first pass metabolism are avoided, the estrogen may be administered in smaller doses. An orodispersible dosage form that has a low dose of estrogen can advantageously help to maintaining therapeutic efficacy, as well as reduce unwanted side effects.

Thus, an orodispersible dosage form is a unique option for contraceptive and/or hormone replacement therapy. It combines the ease of oral administration of tablets with a method of delivery that is akin to transdermal patches, while avoiding both a hepatic first pass and first pass metabolism associated with conventional tablets and even chewable tablets and complexities of application and potential detachment of transdermal patches.

Conventional orodispersible solid dosage forms are generally made using a direct compression method to allow them to achieve the desired disintegration time of about 30 seconds or less. However, direct compression is not considered to be suitable for dosage forms that have a low concentration (e.g., low dose) of the active ingredient(s), such as about 1 wt % or less, or about 0.5 wt % or less, from the standpoint of drug content uniformity. In particular, using direct compression for producing low dose tablets can lead to batches of high and low potency, which is undesirable, because some dosage forms contain either too much or too little of the active ingredient(s).

Typically, a granulation method is used when formulating dosage forms with low concentrations of an active ingredient(s). While granulation can lead to better content uniformity of the active ingredient(s), dosage forms made according to this method do not disintegrate in less than about a minute, or more preferably about 30 seconds or less, in part because granulation involves the use of binders that increase disintegration times.

Additionally, many conventional orodispersible solid dosage forms require peel back aluminum packages (e.g., Alu Alu packaging) due to their fragility and cannot be packaged in conventional and more convenient packaging such as blister packs. This fragility is due to the low compression force that is applied during tableting to decrease the disintegration time.

An orodispersible solid dosage form as disclosed herein overcomes the above-mentioned shortcomings in that in that it uniformly incorporates a low concentration (e.g., low dose) of an active ingredient(s), disintegrates in less than about a minute without the need for chewing and/or swallowing the tablet, preferably about 30 seconds or less, and can have the requisite hardness to be packaged in more conventional packaging, such as blister packs. In addition, this orodispersible solid dosage form can be gluten-free, vegan and contain zero-sugar. In particular, this orodispersible solid dosage form contains an intragranular component that can, for example, constitute from about 40% w/w to about 80% w/w of the orodispersible solid dosage form, as well as an extragranular component. It was found that by combining both direct compression and granulation techniques, a balance between required content uniformity and the disintegration time of less than about a minute, preferably about 30 seconds or less, can be achieved. In addition, this approach makes it possible to use a compression force that provides tablets that can also be more robust for conventional packaging and handling.

Thus, an orodispersible solid dosage form described herein may be a low dose contraceptive and/or hormone replacement therapy dosage form that not only advantageously improves the bioavailability of estrogen, but can also have sufficient uniformity, fast disintegration time, and higher hardness.

The term "orodispersible solid dosage form" as used herein refers to a dosage form that is designed to rapidly disintegrate in the oral cavity when it comes into contact with saliva and to disperse the active ingredient(s) into the saliva so it may be absorbed through the mucosal lining of the oral cavity.

The term "oral administration" as used herein refers to placing the dosage form, as described herein, in the oral cavity to allow for the dosage form to disintegrate in the oral cavity and/or oral mucosa (e.g., lining mucosa). Oral administration, as described herein, includes, but is not limited to, administration to the tongue, sublingual, buccal, and/or sublabial administration, or any combination thereof.

The term administration to the tongue as used herein refers to placing the dosage form on the tongue and allowing it to disintegrate.

The term "sublingual" as used herein refers to the pharmacological route of administration by which the active ingredient(s) diffuses into the blood through tissues under the tongue.

The term "buccal" as used herein refers to the pharmacological route of administration by which the active ingredient(s) diffuses into the blood through tissues of the buccal vestibule including the tongue, the area inside the mouth between the lining of cheek (the buccal mucosa) and the teeth/gums.

The term "sublabial" as used herein refers to the pharmacological route of administration by which the active ingredient(s) is placed between the lip and the gingiva.

A "subject in need thereof" is a subject who is in need of an oral dispersible dosage form, for instance one with a low concentration (e.g., low dose) of an active ingredient. For example, such subject in need thereof may have difficulty swallowing pills or tablets. In an embodiment, the subject in need thereof is a "a female in need thereof" which refers to a human female of child bearing age, a peri-menopausal female, and/or a menopausal female. The female in need thereof may be 35 years of age or younger or may be over the age of 35. The female in need thereof may weigh 180 pounds or less or may weigh over 180 pounds. The female in need thereof may have a body mass index (BMI) of less than 30 kg/m$^2$ or at least 30 kg/m$^2$.

The designation "mcg" refers to micrograms and "mg" to milligrams.

The orodispersible solid dosage form is preferably a fast melt tablet or orally disintegrating tablet as discussed in the FDA Guidance for Industry Orally Disintegrating Tablets dated December 2008, which is incorporated by reference herein. Such tablets are designed to disintegrate or dissolve rapidly on contact with saliva, thus eliminating the need to chew the tablet, swallow an intact tablet, or take the tablet with liquids.

The term "disintegrate", "dissolve" or "disintegration" as used herein refers to disintegration or dissolution as determined in accordance with the methods and procedures described in USP 701 (dated May 1, 2020, available at: https://www.usp.org/sites/default/files/usp/document/harmonization/gen-chapter/april-2019-m99460.pdf), which is incorporated by reference herein.

In an embodiment, the dissolution of the active ingredient(s), for example ethinyl estradiol and norethindrone acetate, can be assessed based on the requirements of United States Pharmacopoeia (USP) 711. For example, not less than 80% (Q) of the labeled amount of the first and/or second active ingredient(s) dissolve in 30 minutes or in 15 minutes, in accordance with the performance tests described in (USP) 711, with the modification that the acetate buffer has a pH of 4.5.

The rapid disintegration as used herein is less than about 60 seconds. For instance, it can be about 55 seconds or less, about 50 seconds or less, about 45 seconds or less, about 40 seconds or less, about 35 seconds or less, or, more preferably based on the FDA Guidance for Industry, about 30 seconds or less.

In some embodiments, the orodispersible solid dosage form described herein disintegrates in about 30 second or less, or about 29 seconds or less, or about 28 seconds or less, or about 27 seconds or less, or about 26 seconds or less, or about 25 seconds or less, about 24 seconds or less, or about 23 seconds or less, or about 22 seconds or less, or about 21 seconds or less, or about 20 seconds or less, or about 15 seconds or less, or about 10 seconds or less. In some embodiments, orodispersible solid dosage form disintegrates in about 1 second to about 30 seconds, about 1 second to about 29 seconds, or about 5 seconds to about 29 seconds, or about 10 seconds to about 29 seconds, or about 15 seconds to about 29 seconds, or about 20 seconds to about 29 seconds. Generally, the orodispersible solid dosage form are formulated to be taken without water.

As mentioned above, the orodispersible solid dosage form comprises an intragranular component and an extragranular component. The intragranular component can constitute from about 40% w/w to about 80% w/w, or about 42% w/w to about 78% w/w, or about 44% w/w to about 74% w/w of the orodispersible solid dosage form. In an embodiment, the intragranular component constitutes at least about 40% w/w, or at least about 41% w/w, or at least about 42% w/w, or at least about 43% w/w, or at least about 44% w/w, or at least about 45% or w/w, or at least about 46% w/w, or at least about 47%, w/w, or at least about 48% w/w, or at least about 49% w/w, or at least about 50% w/w, or at least about 51% w/w, or at least about 52% w/w, or at least about 53% w/w, but not more than 55% w/w, or any amount therebetween. In an embodiment, the intragranular component constitutes at least about 62% w/w, or at least about 65% w/w, or at least about 68% w/w, or at least about 69% w/w, or at least about 70% w/w, or at least about 71% w/w, or at least about 72% w/w, or at least about 73% w/w, or at least about 74% w/w, or at least about 75% w/w, or at least about 76% w/w, but not more than about 80% w/w of the orodispersible solid dosage form, or any amount therebetween.

The extragranular component can constitute from about 20% w/w to about 60% w/w, or about 22% w/w to about 48% w/w, or about 26% w/w to about 56% w/w of the orodispersible solid dosage form. In an embodiment, the extragranular component constitutes at least about 20% w/w, or at least about 22% w/w, at least about 24% w/w, at least about 26% w/w, at least about 28% w/w, at least about 30% w/w, at least about 32% w/w, at least about 34% w/w, but not more than 40% w/w, or any amount therebetween. In an embodiment, the extragranular component constitutes at least about 40% w/w, or at least about 42% w/w, at least about 44% w/w, at least about 46% w/w, at least about 48% w/w, at least about 50% w/w, at least about 52% w/w, at least about 53% w/w, at least about 54% w/w, at least about 56% w/w, at least about 58% w/w, but not more than 60% w/w, or any amount therebetween.

In an embodiment, the orodispersible solid dosage form comprises: a first active ingredient, and optionally a second active ingredient, at least one diluent, at least one disintegrant and at least one binder. In an embodiment, the first active ingredient, and optionally, a second active ingredient, as described herein, may be added to the intragranular component and/or the extragranular component. In an embodiment, the first active ingredient and the second active ingredient are added to the intragranular component. In an embodiment, the first active ingredient is added to the intragranular component and the second active ingredient is added to the intragranular component or the extragranular component, or both the intragranular component and the extragranular component. In an embodiment, the intragranular component comprises: at least one intragranular diluent, at least one intragranular disintegrant, and at least one intragranular binder.

The first active ingredient is an active ingredient which is intended to be included in the formulation as a low concentration (e.g., low dose) active ingredient. For example, the content of the first active ingredient is 0.5% w/w or less, or 0.4% w/w or less, or 0.3% w/w or less, or 0.2% w/w or less or 0.1% w/w or less, or 0.075% w/w or less, or 0.05% w/w or less, or 0.025% w/w or less, but not less than 0.0025%, or preferably not less than 0.001%, or any amount therebetween, based on the total weight of the dosage form. In an embodiment, the content of the first active ingredient is about 0.001% w/w to about 0.5% w/w, or about 0.001% w/w to about 0.4% w/w, or about 0.001% w/w to about 0.3% w/w, or about 0.001% w/w to about 0.25% w/w, or about 0.001% w/w to about 0.2% w/w, or about 0.001% w/w to about 0.15% w/w, or about 0.001% w/w to about 0.01% w/w, or 0.001% w/w to about 0.05% w/w, or about 0.001% w/w to about 0.04% w/w, or about 0.001% w/w to about 0.03% w/w, or about 0.001% w/w to about 0.025% w/w, or about 0.001% w/w to about 0.02% w/w, or about 0.001% w/w to about 0.015% w/w, or about 0.001% w/w to about 0.01% w/w, or 0.002% w/w to about 0.5% w/w, or about 0.002% w/w to about 0.4% w/w, or about 0.002% w/w to about 0.3% w/w, or about 0.002% w/w to about 0.25% w/w, or about 0.002% w/w to about 0.2% w/w, or about 0.002% w/w to about 0.15% w/w, or about 0.002% w/w to about 0.1% w/w, 0.002% w/w to about 0.05% w/w, or about 0.002% w/w to about 0.04% w/w, or about 0.002% w/w to about 0.03% w/w, or about 0.002% w/w to about 0.025% w/w, or about 0.002% w/w to about 0.02% w/w, or about 0.002% w/w to about 0.015% w/w, or about 0.002% w/w to about 0.01% w/w, or 0.0025% w/w to about 0.5% w/w, or about 0.0025% w/w to about 0.4% w/w, or about 0.0025% w/w to about 0.3% w/w, or about 0.0025% w/w to about 0.25% w/w, or about 0.0025% w/w to about 0.2% w/w, or about 0.0025% w/w to about 0.15% w/w, or about 0.0025% w/w to about 0.1% w/w, or about 0.0025% w/w to about 0.05%, or about 0.0025% w/w to about 0.005%, or 0.003% w/w to about 0.5% w/w, or about 0.003% w/w to about 0.4% w/w, or about 0.003% w/w to about 0.3% w/w, or about 0.003% w/w to about 0.25% w/w, or about 0.003% w/w to about 0.2% w/w, or about 0.003% w/w to about 0.15% w/w, or about 0.003% w/w to about 0.01% w/w, or about 0.0025% w/w to about 0.005% w/w, or about 0.0025% w/w to about 0.004% w/w or 0.003% w/w to about 0.05% w/w, or about 0.003% w/w to about 0.04% w/w, or about 0.003% w/w to about 0.03% w/w, or about 0.003% w/w to about 0.025% w/w, or about 0.003% w/w to about 0.02% w/w, or about 0.003% w/w to about 0.015% w/w, or about 0.003% w/w to about 0.01% w/w, or about 0.005% w/w to about 0.5% w/w, or about 0.005% w/w to about 0.4% w/w, or about 0.005% w/w to about 0.3% w/w, or about 0.005% w/w to about 0.25% w/w, or about 0.005% w/w to about 0.2% w/w, or about 0.005% w/w to about 0.15% w/w, about 0.005% w/w to about 0.1% w/w, or about 0.005% w/w to about 0.05% w/w, or about 0.005% w/w to about 0.04% w/w, or about 0.005% w/w to about 0.03% w/w, or about 0.005% w/w to about 0.025% w/w, or about 0.005% w/w to about 0.02% w/w, or about 0.005% w/w to about 0.015% w/w, about 0.005% w/w to about 0.01% w/w, or about 0.0250% w/w to about 0.50% w/w, or about 0.0250% w/w to about 0.05% w/w, or about 0.025% w/w to about 0.4% w/w, or about 0.025% w/w to about 0.3% w/w, or about 0.025% w/w to about 0.2% w/w, or about 0.025% w/w to about 0.1% w/w, or about 0.025% w/w to about 0.05% w/w, or about 0.025% w/w to about 0.035% w/w, or about 0.1% w/w to about 0.5% w/w, or about 0.1% w/w to about 0.4% w/w, or about 0.1% w/w to about 0.3% w/w, or about 0.1% w/w to about 0.2% w/w based on the total weight of the dosage form. In an embodiment, the content of the first active ingredient is at least about 0.001% w/w, or at least about 0.0015% w/w, or at least about 0.002% w/w, or at least about 0.0025% w/w, or at least about 0.003% w/w, or at least about 0.0035% w/w, at least about 0.004% w/w, or at least about 0.0045% w/w, or at least about 0.005% w/w, or at least about 0.01% w/w, or at least about 0.02% w/w, or at least about 0.03% w/w, or at least about 0.04% w/w, or at least about 0.05% w/w, or at least about 0.06% w/w, or at least about 0.07% w/w, or at least about 0.08% w/w, or at least about 0.09% w/w, or at least about 0.1% w/w, or at least about 0.2%, or at least about 0.3%, or at least about 0.4% but not greater than 0.5% w/w.

Non-limiting examples of the first active ingredient are analgesics, alpha blockers, anti-allergy agents, anti-asthma agents, allergic rhinitis, chronic urticaria, anti-inflammatory agents, antacids, anthelmintics, anti-arrhythmic agents, anti-arthritis, anti-bacterial agents, anti-anxiety agents, anti-coagulants, anti-depressants, anti-diabetics, anti-diarrheals, anti-diuretics, anti-epileptics, anti-fungal agents, anti-gout agents, anti-hypertensive agents, anti-incontinence agents, anti-insomnia agents, anti-malarials, anti-migraine agents, anti-muscarinic agents, anti-neoplastic and immunosuppressants, anti-protozoal agents, anti-rheumatics, anti-rhinitis agents, anti-spasmatic agents, anti-thyroid agents, antivirals, anxiolytics, sedatives, hypnotics and neuroleptics, beta-blockers, anti-benign hyperplasia (BHP) agents, cardiac inotropic agents, corticosteroids, cough suppressants, cytotoxics, decongestants, diabetic gastric stasis, diuretics, enzymes, anti-parkinsonian agents, gastro-intestinal agents, histamine receptor antagonists, infertility agents, endometriosis agents, hormone replacement therapy, lipid regulating agents, local anesthetics, neuromuscular agents, nitrates and anti-anginal agents, menstrual disorder agents, motion sickness agents, anti-inflammatory agents, anti-nausea agents, movement disorder agents, nutritional agents, opioid analgesics, oral vaccines, proteins, peptides and recombinant drugs, prevention of chemotherapy induced and post-operative nausea and vomiting proton pump inhibitors, anti-schizophrenia agents, sex hormones and contraceptives, seizure/panic disorder agents, sexual dysfunction (male and female) agents, spermicides, stimulants voiding dysfunction agents, and/or veterinary medicines.

In an embodiment, the first active ingredient may be an estrogen. Estrogens which may be used in the present invention include, for example, ethinyl estradiol, 17β-estradiol, 17β-estradiol-3-acetate, mestranol, conjugated estrogens, USP and estrone or salts thereof. In an embodiment, the estrogen is ethinyl estradiol. The amount of estrogen used is described herein as that which is "equivalent" in estrogenic potency to an amount of ethinyl estradiol. The equivalent estrogenic potency of an estrogen to ethinyl estradiol may be readily determined by one of ordinary skill in the art.

In an embodiment, the orodispersible solid dosage form contains an estrogen in an amount equivalent to about 0.001% w/w to about 0.5%, or about 0.001% w/w to about 0.05% w/w, or about 0.0015% w/w to about 0.5%, or about 0.0015% w/w to about 0.05%, or about 0.002% w/w to about 0.5%, or about 0.002% w/w to about 0.05%, or about 0.0025% w/w to about 0.5% w/w, or about 0.0025% w/w to about 0.4% w/w, or about 0.0025% w/w to about 0.3% w/w, or about 0.0025% w/w to about 0.2% w/w, about 0.0025% w/w to about 0.1% w/w, or about 0.0025% w/w to about 0.05% w/w, or about 0.0025% w/w to about 0.04% w/w, or about 0.0025% w/w to about 0.03% w/w, or about 0.0025% w/w to about 0.025% w/w, or about 0.0025% w/w to about 0.02% w/w, or about 0.0025% w/w to about 0.015% w/w, or about 0.0025% w/w to about 0.01% w/w, or about 0.0025% w/w to about 0.005% w/w, or about 0.0025% w/w to about 0.004% w/w, or about 0.003% w/w to about 0.5%, or about 0.003% w/w to about 0.4% w/w, or about 0.003% w/w to about 0.3% w/w, or about 0.003% w/w to about 0.2% w/w, about 0.003% w/w to about 0.1% w/w, or about 0.003% w/w to about 0.05%, or about 0.003% w/w to about 0.04% w/w, or about 0.003% w/w to about 0.03%, or about 0.003% w/w to about 0.02%, or about 0.003% w/w to about 0.01%, or 0.0035% w/w to about 0.05%, about 0.004% w/w to about 0.05%, about 0.0045% w/w to about 0.05%, or about 0.005% w/w to about 0.5% w/w, or about 0.005% w/w to about 0.4% w/w, or about 0.005% w/w to about 0.3% w/w, or about 0.005% w/w to about 0.25% w/w, or about 0.005% w/w to about 0.2% w/w, or about 0.005% w/w to about 0.15% w/w, about 0.005% w/w to about 0.1% w/w, or about 0.005% w/w to about 0.05% w/w, or about 0.005% w/w to about 0.04% w/w, or about 0.005% w/w to about 0.03% w/w, or about 0.005% w/w to about 0.025% w/w, or about 0.005% w/w to about 0.02% w/w, or about 0.005% w/w to about 0.015% w/w, about 0.005% w/w to about 0.01% w/w, or about 0.025% w/w to about 0.5% w/w, or about 0.025% w/w to about 0.4% w/w, or about 0.025% w/w to about 0.3% w/w, or about 0.025% w/w to about 0.2% w/w, or about 0.025% w/w to about 0.1% w/w, or about 0.025% w/w to about 0.05% w/w, or about 0.025% w/w to about 0.0355% w/w, or about 0.10% w/w to about 0.5% w/w, or about 0.1% w/w to about 0.4% w/w, or about 0.10% w/w to about 0.30% w/w, or about 0.10% w/w to about 0.2% w/w of ethinyl estradiol (or an ethinyl estradiol prodrug in an amount equivalent in potency to ethinyl estradiol) based on the total weight of the dosage form.

In an embodiment, the orodispersible solid dosage form contains an estrogen in an amount equivalent to about 0.5 mcg to about 50 mcg, or about 1 mcg to about 50 mcg, or about 1 mcg to about 30 mcg, or about 1 mcg to about 25 mcg, or about 1 mcg to about 20 mcg, or about 1 mcg to about 15 mcg, or about 1 mcg to about 10 mcg, or about 1 mcg to about 5 mcg, or about 1 mcg to about 4.5 mcg, or about 2 mcg to about 25 mcg, or about 2 mcg to about 20 mcg, or about 2 mcg to about 15 mcg, or about 2 mcg to about 10 mcg, or about 2 mcg to about 5 mcg, or about 2 mcg to about 4.5 mcg, or about 5 mcg to about 25 mcg, or about 5 mcg to about 20 mcg, or about 5 mcg to about 15 mcg of ethinyl estradiol (or an ethinyl estradiol prodrug in an amount equivalent in potency to ethinyl estradiol), and any amount in between. In an embodiment, the orodispersible solid dosage form contains about 1 mcg, or about 1.5 mcg or about 2 mcg, about 2.5 mcg, or about 3 mcg, or about 3.5 mcg, or about 4 mcg, or about 4.5 mcg, or about 5 mcg, or about 7.5 mcg, or about 10 mcg, or about 12.5 mcg, or about 15 mcg, or about 20 mcg, or about 25 mcg, or about 30 mcg, or about 35 mcg, or about 40 mcg, or about 45 mcg, or about 50 mcg, or any amount therebetween of ethinyl estradiol (or an ethinyl estradiol prodrug in an amount equivalent in potency to ethinyl estradiol). In an embodiment, the estrogen is included in the intragranular component and/or the extragranular component.

In an embodiment, at least 5% of the ethinyl estradiol in the orodispersible solid dosage form that is administered is absorbed into and/or through the oral mucosa and/or tongue prior to entry into the bloodstream, or at least 10%, or at least 15%, or at least 20%, or at least 30%, or at least 40%, or at least 50%, or at least 60%, or at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% or any amount therebetween. Orally administering the orodispersible solid dosage form without water allows for a higher level of absorption into oral mucosa and/or tongue, especially, for example, when the orodispersible solid dosage form is placed on the tongue and allowed to disintegrate on the tongue.

For example, upon oral administration of the dosage form, the oral mucosa can act as a membrane in the oral cavity that can control the release of the drug from the solute state into the bloodstream, e.g., becoming a rate controlling membrane for drug absorption to the blood. Thus, by virtue of the ethinyl estradiol being absorbed into and/or through the oral mucosa and/or tongue, the drug may be stored in the oral mucosa and/or the tongue and then can diffuse into the blood stream thereby avoiding hepatic first pass and first pass metabolism.

The second active ingredient is an active ingredient which may be included in the formulation as a low concentration (e.g., low dose) active ingredient or could be a higher concentration active ingredient. For example, the content of the second active ingredient is about 0.1% w/w to about 30% w/w, or about 0.2% to about 25% w/w, or about 0.3% w/w to about 20% w/w, or about 0.4% to about 15% w/w, or 0.5% w/w to about 10% w/w, or about 10% w/w to about 10% w/w, or about 10% w/w to about 9% w/w, or about 1% w/w to about 8% w/w, or about 1% w/w to about 7% w/w, or about 1% w/w to about 6% w/w, about 1% w/w to about 5% w/w, about 1% w/w to about 4% w/w, or about 1% w/w to about 3% w/w, or about 1% w/w to about 1.5% w/w, or about 1% w/w to about 1.45% w/w, based on the total weight of the dosage form.

Non-limiting examples of the second active ingredient are analgesics, alpha blockers, anti-allergy agents, anti-asthma agents, allergic rhinitis, chronic urticaria, anti-inflammatory agents, antacids, anthelmintics, anti-arrhythmic agents, anti-arthritis, anti-bacterial agents, anti-anxiety agents, anti-coagulants, anti-depressants, anti-diabetics, anti-diarrheals, anti-diuretics, anti-epileptics, anti-fungal agents, anti-gout agents, anti-hypertensive agents, anti-incontinence agents, anti-insomnia agents, anti-malarials, anti-migraine agents, anti-muscarinic agents, anti-neoplastic and immunosuppressants, anti-protozoal agents, anti-rheumatics, anti-rhinitis agents, anti-spasmatic agents, anti-thyroid agents, antivirals, anxiolytics, sedatives, hypnotics and neuroleptics, beta-blockers, anti-benign hyperplasia (BHP) agents, cardiac inotropic agents, corticosteroids, cough suppressants, cytotoxics, decongestants, diabetic gastric stasis, diuretics, enzymes, anti-parkinsonian agents, gastro-intestinal agents, histamine receptor antagonists, infertility agents, endometriosis agents, hormone replacement therapy, lipid regulating agents, local anesthetics, neuromuscular agents, nitrates and anti-anginal agents, menstrual disorder agents, motion sickness agents, anti-inflammatory agents, anti-nausea agents, movement disorder agents, nutritional agents, opioid analgesics, oral vaccines, proteins, peptides and recombinant drugs, prevention of chemotherapy induced and post-operative nausea and vomiting proton pump inhibitors, anti-schizophrenia agents, sex hormones and contraceptives, seizure/panic disorder agents, sexual dysfunction (male and female) agents, spermicides, stimulants voiding dysfunction agents, and/or veterinary medicines.

In an embodiment, the second active ingredient is a progestogen. Progestogens which may be used in the present invention include, for example, progesterone and its derivatives such as 17-hydroxy progesterone esters and 19-nor-17-hydroxy progesterone esters, 17-alpha-ethinyl testosterone, 17-alpha-ethinyl-19-nortestosterone (norethindrone) and derivatives thereof, norethindrone acetate, norgestrel, nogestamate, desogestrel and D-17-beta-acetoxy-17-beta-ethyl-17-alpha-ethinyl-gon-4-en-3-one oxime. Other exemplary progestogens include demegestone, drospirenone, dydrogesterone, gestodene, medrogestone, medroxy progesterone and esters thereof. The amount of progestogen used is described herein as that which is "equivalent" in progestogenic potency to an amount of norethindrone acetate. The equivalent progestogenic potency of a progestogen to norethindrone acetate may be readily determined by one of ordinary skill in the art.

In an embodiment, the orodispersible solid dosage form contains at least one progestogen in an amount equivalent in potency to 0.40% w/w to about 2.2% w/w, or 0.4% w/w to about 1.9% w/w, or about 0.4% w/w to about 1.5% w/w, or about 0.7% w/w to about 2.2% w/w, or about 0.7% w/w to about 1.9% w/w, or about 0.7% w/w to about 1.5% w/w, or about 1% w/w to about 2.2%, or about 1% w/w to about 1.9% w/w or about 1% w/w to about 1.5% w/w, or about 1% w/w to about 1.45% w/w of norethindrone acetate or norethindrone based on the total weight of the dosage form.

In an embodiment, the orodispersible solid dosage form also contains at least one progestogen in an amount equivalent in potency to about 0.3 mg to about 1.5 mg, or about 0.5 mg to about 1 mg of norethindrone acetate or norethindrone. In some embodiments, the orodispersible solid dosage form contains about 0.3 mg, or about 0.4 mg, or about 0.5 mg, or about 0.6 mg, or about 0.7 mg, or about 0.8 mg, or about 0.9 mg, or about 1.0 mg, or about 1.1 mg, or about 1.2 mg, or about 1.3 mg, or about 1.4 mg, or 1.5 mg, or any amount therebetween of norethindrone acetate or norethindrone. In an embodiment the progestogen is included in the intragranular component or the extragranular component.

Examples of at least one diluent that may be used in the orodispersible dosage forms as disclosed herein include microcrystalline cellulose, dibasic calcium phosphate, glucose, dextrose, fructose, lactose, mannitol and/or sorbitol. In an embodiment, at least one diluent that is included is microcrystalline cellulose. In an embodiment, at least one diluent that is included is mannitol. In an embodiment, the orodispersible solid dosage form comprises at least two diluents. In an embodiment, these at least two diluents are microcrystalline cellulose and mannitol. In an embodiment, the diluent content in the orodispersible solid dosage form is about 80% w/w to about 95% w/w, or about 82% w/w to about 93% w/w, or about 84% w/w to about 89% w/w.

In an embodiment, the orodispersible solid dosage form comprises at least about 30% w/w, or at least about 35% w/w, or at least about 40% w/w, or at least about 45% w/w, or at least about 50% w/w, or at least about 55% w/w, or at least about 60% w/w, or at least about 65% w/w or more, but not more than 80% w/w, or any amount therebetween of mannitol. In an embodiment, the orodispersible solid dosage form comprises about at least about 10% w/w, or at least about 15% w/w, or at least about 20% w/w, or at least about 25% w/w, or at least about 30% w/w or more, at least about 35% w/w or more, but not more than 40% w/w, or any amount therebetween of microcrystalline cellulose.

Various types of disintegrants may be used in the orodispersible dosage forms as disclosed herein. For example, at least one disintegrant that may be used is a superdisintegrant, such as croscarmellose sodium, crospovidone and/or sodium starch glycolate ("SSG"). In an embodiment, the disintegrant may be Starch NF, Starch 1500, alginic acid, microcrystalline cellulose and/or any other components known in the art which aid disintegration. In an embodiment, the orodispersible solid dosage form comprises about 1% w/w to about 45% w/w, or about 2% to about 43%, or about 3% to 40%, or about 4% to about 40%, or about 5% to about 40%, or about 10% to about 40%, or about 20% to about 40%, or about 30% to about 40% or about 35% to about 40% of a disintegrant. In an embodiment, the orodispersible solid dosage form comprises at least about 2% w/w, or at least about 2.5% w/w, or at least about 3% w/w, or at least about 3.5% w/w, or at least about 4% w/w, or at least about 4.5% w/w, or at least about 5% w/w, or at least about 5.5% w/w, or at least about 6% w/w, or at least about 6.5% w/w, at least about 9% w/w, at least about 10% w/w, or at least about 15% w/w, or at least about 20% w/w, or at least about 25% w/w, or at least about 30% w/w, or at least about 35% w/w, or at least about 36% w/w, or at least about 37% w/w, or at least about 38% w/w, or at least about 39% w/w or at least about 40% w/w, or at least about 41% w/w or at least about 42% w/w, or at least about 43% w/w, or at least about 44% w/w, but not more than 45% w/w of the at least one disintegrant. In an embodiment, the orodispersible solid dosage form comprises about 1% w/w to about 10% w/w, or about 2% w/w to about 9% w/w, or 2% w/w to about 8%, or about 2% w/w to about 7%, or about 3% w/w to about 8% w/w, or about 3% w/w to about 7% or about or about 4% w/w to about 7% w/w, or about 4% w/w to about 6% w/w of the at least one disintegrant, for instance a superdisintegrant. In an embodiment, the orodispersible solid dosage form comprises at least about 2% w/w, or at least about 2.5% w/w, or at least about 3% w/w, or at least about 3.5% w/w, or at least about 4% w/w, or at least about 4.5% w/w, or at least about 5% w/w, or at least about 5.5% w/w, or at least about 6% w/w, or at least about 6.5% w/w, but not more than 9% w/w of the at least one disintegrant, for instance a superdisintegrant.

Various types of binders may be used in the orodispersible dosage forms as disclosed herein. Such binders include natural binders, synthetic/semisynthetic polymers, and sugars. For example, at least one binder may be a dry binder and/or a wet binder. In an embodiment, the binder may be sucrose, liquid glucose, acacia, tragacanth, gelatin, alginic acid, cellulose, methyl cellulose, ethyl cellulose, hydroxy propyl methyl cellulose (HPMC), hydroxy propyl cellulose, sodium carboxy methyl cellulose, polyethylene glycol (PEG), polyvinyl alcohols, or polymethacrylates. In an embodiment, the dry binder is a starch. In an embodiment, the starch is Starch 1500® or a partially pregelatinized starch or a fully pregelatinized starch or a starch paste. In an embodiment, the wet binder is polyvinyl pyrrolidone or povidone. In an embodiment, the orodispersible solid dosage form comprises about 0.5% w/w to about 10% w/w, or about 2% w/w to about 9% w/w, or 2% w/w to about 8%, or about 2% w/w to about 7%, or about 3% w/w to about 8% w/w, or about 3% w/w to about 7% or about or about 4% w/w to about 7% w/w, or about 4% w/w to about 6% w/w of the at least one binder. In an embodiment, the orodispersible solid dosage form comprises at least about 2% w/w, or at least about 2.5% w/w, or at least about 3% w/w, or at least about 3.5% w/w, or at least about 4% w/w, or at least about 4.5% w/w, or at least about 5% w/w, or at least about 5.5% w/w, or at least about 6% w/w, or at least about 6.5% w/w, but not more than 9% w/w, or any amount therebetween of the at least one binder.

In an embodiment, the intragranular component can include at least one diluent, at least one disintegrant, and at least one binder. The extragranular component can include at least one diluent and at least one disintegrant.

In an embodiment, the at least one intragranular diluent is a diluent as described herein. In an embodiment, the at least one intragranular diluent is microcrystalline cellulose. In an embodiment, the at least one intragranular diluent is mannitol. In an embodiment, the at least one intragranular diluent is a combination of microcrystalline cellulose and mannitol.

In an embodiment, the at least one intragranular diluent content in the intragranular component is from about 80% w/w to about 97% w/w, or about 83% w/w to about 97% w/w, or about 84% w/w to about 97% w/w, or about 87% w/w to about 97% w/w, or about 89% w/w to about 95% w/w of the intragranular component. In an embodiment, this content is at least about 80% w/w, at least about 81% w/w, at least about 82% w/w, at least about 83% w/w, at least about 84% w/w, at least about 85% w/w, or at least about 86% w/w, or at least about 87% w/w, or at least about 88% w/w, or at least about 89% w/w, or at least about 90% w/w, or at least about 91% w/w, or at least about 92% w/w, or at least about 93% w/w, or at least about 94% w/w, or at least about 95% w/w, or at least about 96% w/w, but not more than about 97% w/w, or any amount therebetween of the intragranular component.

In an embodiment, the at least one intragranular disintegrant is a disintegrant described herein. In an embodiment, the at least one intragranular disintegrant is croscarmellose sodium. In an embodiment, the at least one intragranular disintegrant is sodium starch glycolate.

In an embodiment, the at least one intragranular disintegrant content, for instance for a superdisintegrant, in the intragranular component is from about 2% w/w to about 5% w/w, or about 2.2% w/w to about 4.5% w/w, or about 2.3% w/w to about 4.1% w/w, or about 2.4% w/w to about 3.8% w/w, or about 2.5% w/w to about 3.5% w/w of the intragranular component. In an embodiment, this content is at least about 2% w/w, or at least about 2.1% w/w, or at least about 2.2% w/w, or at least about 2.3% w/w, or at least about 2.4% w/w, or at least about 2.5% w/w, or at least about 2.6% w/w, or at least about 2.7% w/w, or at least about 2.8% w/w, or at least about 2.9% w/w, or at least about 3.0% w/w, or at least about 3.1% w/w, or at least about 3.2% w/w, or at least about 3.3% w/w or at least about 3.4% w/w, or at least about 3.5% w/w, or at least about 3.6% w/w, or about at least 3.7% w/w, or at least about 3.8% w/w, or at least about 3.9% w/w, at least about 4.0% w/w, or at least about 4.2% w/w, or at least about 4.4% w/w, or at least about 4.6% w/w, or at least about 4.8%, or at least about 5.0% w/w, or at least about 5.2% w/w, or at least about 5.4% w/w, or at least about 5.6% w/w, or at least about 5.8% w/w, but not more than about 6.0% w/w, or any amount therebetween of the intragranular component. In an embodiment, this content is at least about 2% w/w, or at least about 2.1% w/w, or at least about 2.2% w/w, or at least about 2.3% w/w, or at least about 2.4% w/w, or at least about 2.5% w/w, or at least about 2.6% w/w, or at least about 2.7% w/w, or at least about 2.8% w/w, or at least about 2.9% w/w, or at least about 3.0% w/w, or at least about 3.1% w/w, or at least about 3.2% w/w, or at least about 3.3% w/w or at least about 3.4% w/w, or at least about 3.5% w/w, or at least about 3.6% w/w, or about at least 3.7% w/w, or at least about 3.8% w/w, or at least about 3.9% w/w, at least about 4.0% w/w, or at least about 4.2% w/w, or at least about 4.4% w/w, or at least about 4.6% w/w, or at least about 4.8% w/w, but not more than about 5.0% w/w, or any amount therebetween of the intragranular component. In an embodiment, this content is at least about 2% w/w, or at least about 2.1% w/w, or at least about 2.2% w/w, or at least about 2.3% w/w, or at least about 2.4% w/w, or at least about 2.5% w/w, or at least about 2.6% w/w, or at least about 2.7% w/w, or at least about 2.8% w/w, or at least about 2.9% w/w, but not more than about 3.0% w/w, or any amount therebetween of the intragranular component. In an embodiment, this content is at least about 2.4% w/w, or at least about 2.5% w/w, or at least about 2.6% w/w, or at least about 2.7% w/w, or at least about 2.8% w/w, or at least about 2.9% w/w, or at least about 3% w/w, or at least about 3.1% w/w, or at least about 3.2% w/w, or at least about 3.3% w/w, or at least about 3.4% w/w, or at least about 3.5% w/w, or at least about 3.6% w/w, or at least about 3.7% w/w, or at least about 3.8% w/w, or at least about 3.9% w/w but not more than about 4.0% w/w, or any amount therebetween of the intragranular component.

In an embodiment, the at least one intragranular binder is a binder as described herein. In an embodiment, the at least one intragranular binder is starch, Starch 1500®, a partially pregelatinized starch, a fully pregelatinized starch and/or povidone.

In an embodiment, the at least one intragranular binder content in the intragranular component is from about 0.2% w/w to about 7% w/w, or about 0.5% w/w to about 6.5% w/w, or about 0.8% w/w to about 6% w/w, or about 0.9% w/w to about 5.6% w/w, or about 1% w/w to about 5.4% w/w of the intragranular component. In an embodiment, this content is at least about 0.2% w/w, or at least about 0.3% w/w, or at least about 0.4% w/w, or at least about 0.5% w/w, or at least about 0.6% w/w, or at least about 0.7% w/w, or at least about 0.8% w/w, or at least about 0.9% w/w, or at least about 1% w/w, or at least about 1.1% w/w, or at least about 1.2% w/w, or at least about 1.3% w/w, or at least about 1.5% w/w, or at least about 1.8% w/w, or at least about 2.0% w/w, or at least about 2.1% w/w, or at least about 2.2% w/w, or at least about 2.3% w/w, or at least about 2.4% w/w, or at least about 2.5% w/w, or at least about 2.8% w/w, or at least about 3.1% w/w, or at least about 3.4% w/w, or at least about 3.7% w/w, or at least about 4.1% w/w, or at least about 4.4% w/w, or at least about 4.7% w/w, or at least about 4.9% w/w, or at least about 5% w/w, or at least about 5.1% w/w, or at least about 5.2% w/w, or at least about 5.3% w/w, or at least about 5.4% w/w, or at least about 5.5% w/w, or at least about 5.8% w/w, but not more than about 6% w/w, or any amount therebetween of the intragranular component. In an embodiment, the at least one intragranular binder content in the intragranular component is at least about 0.2% w/w, at least about 0.3% w/w, or at least about 0.4% w/w, or at least about 0.5% w/w, or at least about 0.6% w/w, at least about 0.7% w/w, or at least about 0.8% w/w, or at least about 0.9% w/w, or at least about 1% w/w, or at least about 1.1% w/w, or at least about 1.2% w/w, or at least about 1.3% w/w, or at least about 1.5% w/w, or at least about 1.8% w/w, or at least about 2.0% w/w, or at least about 2.1% w/w, or at least about 2.2% w/w, or at least about 2.3% w/w, but not more than about 2.4% w/w, or any amount therebetween of the intragranular component. In an embodiment, the at least one intragranular binder content in the intragranular component is at least about 4.7% w/w, or at least about 4.9% w/w, or at least about 5% w/w, or at least about 5.1% w/w, or at least about 5.2% w/w, or at least about 5.3% w/w, or at least about 5.4% w/w, or at least about 5.5% w/w, but not more than about 5.6% w/w, or any amount therebetween of the intragranular component.

In an embodiment, the extragranular component comprises: at least one extragranular diluent, and at least one extragranular disintegrant. In an embodiment, the extragranular component comprises: at least one extragranular diluent, at least one extragranular disintegrant and at least one extragranular binder.

In an embodiment, the at least one extragranular diluent is a diluent as described herein. In an embodiment, the at least one intragranular diluent and the at least one extragranular diluent are the same. In an embodiment, the at least one intragranular diluent and the at least one extragranular diluent are different.

In an embodiment, the least one extragranular diluent content in the extragranular component is from about 70% w/w to about 88% w/w, or about 74% w/w to about 87% w/w, or about 76% w/w to about 86% w/w of the extragranular component. In an embodiment, this content is at least about 70% w/w, or at least about 71% w/w, or at least about 72% w/w, or at least about 73% w/w, or at least about 74% w/w, or at least about 75% w/w, or about 76% w/w, or about 77% w/w, or about 78% w/w, or about 79% w/w, or at least about 80% w/w, or at least about 81% w/w, or at least about 82% w/w, or at least about 83% w/w, or at least about 84% w/w, or at least about 85% w/w, or at least about 86% w/w, but not more than about 87% w/w, or any amount therebetween of the extragranular component.

In an embodiment, the at least one extragranular disintegrant is the disintegrant as described herein. In an embodiment, the at least one intragranular disintegrant and the at least one extragranular disintegrant are the same. In an embodiment, the at least one intragranular disintegrant and the at least one extragranular disintegrant are different.

In an embodiment, the at least one extragranular disintegrant content in the extragranular component is from about 4% w/w to about 12% w/w, or about 4% w/w to about 11% w/w, or about 4% w/w to about 10% w/w, or about 5% w/w to about 12% w/w, or about 50% w/w to about 110% w/w, or about 50% w/w to about 10% w/w, or about 6% w/w to about 12% w/w, or about 6% w/w to about 11% w/w, or about 6% w/w to about 10% w/w, or about 6% w/w to about 9% w/w of the extragranular component. In an embodiment, this content is at least about 4% w/w, or at least about 4.5% w/w, or at least about 5% w/w, or at least about 5.5% w/w, or at least about 6% w/w, or at least about 6.5% w/w, or at least about 7% w/w, or at least about 7.25% w/w, or at least about 7.5% w/w, or at least about 8% w/w, or at least about 8.5% w/w, or at least about 9% w/w, or at least about 9.5% w/w, or at least about 10% w/w, or at least about 10.5% w/w, or at least about 10.75%, or at least about 110% w/w, or at least about 11.5% w/w, but not more than about 12% w/w, or any amount therebetween of the extragranular component.

In an embodiment, the at least one extragranular binder is the binder as described herein. In an embodiment, the at least one intragranular binder and the at least one extragranular binders are the same. In an embodiment, the at least one intragranular binders and the at least one extragranular binders are different.

In an embodiment, the at least one extragranular binder content in the extragranular component is from about 3% w/w to about 12% w/w, or about 3.5% w/w to about 110% w/w, or about 4% w/w to about 10% w/w of the extragranular component. In an embodiment, this content is at least about 3% w/w, or at least about 3.5% w/w, or at least about 4% w/w, or at least about 4.2% w/w, or at least about 4.3% w/w, or at least about 4.4% w/w, or at least about 4.5% w/w, or at least about 4.75% w/w, or at least about 5% w/w, or at least about 5.5% w/w, or at least about 6% w/w, or at least about 6.5% w/w, or at least about 7% w/w, or at least about 7.5% w/w, or at least about 8% w/w, or at least about 8.5% w/w, or at least about 9% w/w, but not more than about 10% w/w, or any amount therebetween of the extragranular component.

In an embodiment, the orodispersible solid dosage form may comprise at least one additional agent including, but not limited to, a lubricant, an antioxidant, a flavoring agent, a sweetener, or a coloring agent. In an embodiment, the intragranular component and/or the extragranular component comprises at least one of these additional agents.

In an embodiment, the orodispersible solid dosage form are uncoated. In an embodiment, the orodispersible solid dosage form may be coated with any suitable coating agent well known in the art in at least one coating layer, provided that the desired disintegration time can be maintained. For example, a suitable coating may be used to provide taste masking.

In practicing the contraceptive and/or hormone replacement methods of the present invention, the orodispersible solid dosage form, as described herein, is orally administered. For example, the orodispersible solid dosage form may be placed on the tongue. In some of the methods of the present invention, the estrogen should be contacted with the patient's oral mucosa, whereby at least a portion of the estrogen is absorbed through the patient's oral mucosa. An orodispersible solid dosage form should be capable of diffusing a significant portion of the estrogen into the oral mucosa in the oral cavity. In some embodiments, the orodispersible solid dosage will result in immediate or rapid release of the estrogen in the oral cavity.

In an embodiment, the orodispersible solid dosage form, as described herein, is administered to a female in need thereof by sublingual, buccal or sublabial administration for a contraceptive and/or hormone replacement therapy. In an embodiment, the orodispersible solid dosage form is continuously administered without administering a placebo. In an embodiment, the orodispersible solid dosage form is administered for a consecutive period of at least about 21 days, about 22 days, about 23 days, about 24 days, about 25 days, about 26 days, about 27 days, about 28 days, about 29 days, about 30 days, about 31 days, about 42 days, about 48 days, about 59 days, about 60 days, about 61 days, about 62 days, about 63 days, about 72 days, about 84 days, about 90 days, about 91 days, about 92 days, about 96 days, about 105 days, about 120 days, about 126 days, about 144 days, about 147 days, about 151 days, about 152 days, about 153 days, about 168 days, about 181 days, about 182 days, about 184 days, about 189 days, about 192 days, about 210 days, about 212 days, about 213 days, about 214 days, about 216 days, about 231 days, about 240 days, about 252 days, about 264 days, about 273 days, about 274 days, about 288 days, about 294 days, about 304 days, about 305 days, about 312 days, about 315 days, about 334 days, about 335 days, about 336 days, about 357 days, about 360 days, about 365 days or about 366 days, followed by administration of a placebo for at most 7 days. In an embodiment, the orodispersible solid dosage form is administered once daily.

In an embodiment, a process for preparing an orodispersible solid dosage form as described herein comprises Fluid bed granulation and drying, blending with extragranular components and direct compression. In an embodiment, the process includes:

(a) preparing a granulating solution by dispersing a first active ingredient, and optionally a second active ingredient, in a solvent;

(b) granulating the granulating solution with an intragranular component comprising at least one intragranular diluent, at least one intragranular disintegrant and at least one intragranular binder;

(c) blending step (b) with an extragranular component, wherein the extragranular component comprises at least one extragranular diluent and at least one extragranular disintegrant, and optionally, an extragranular binder;

(d) compressing the blended ingredients from step (c) into an orodispersible solid dosage form.

In an embodiment, the granulating solution comprises at least one solvent such as ethanol, water or a combination thereof.

The compression force that is applied when compressing the blended ingredients should produce a tablet that allows it to maintain the desired disintegration time. The intragranular/extragranular technique as described herein allows various different compression forces to be used and still provide the disintegration time of about 30 seconds or less.

In an embodiment, the orodispersible solid dosage form is a tablet. In an embodiment, the tablets can be packaged in conventional packaging, including but not limited to blister packs.

In an embodiment, the orodispersible solid dosage form, as described herein, has a weight between about 40 mg and about 500 mg, or about 45 mg and about 300 mg, or about 50 mg and about 150 mg, or about 70 mg and about 150 mg, or about 70 mg and about 100 mg, 70 mg and about 90 mg, or about 80 mg and about 90 mg and any weight in between. In some embodiments, the solid dosage form is about 40 mg, about 45 mg, about 50 mg, about 55 mg, about 60 mg, about 65 mg, about 70 mg, about 75 mg, about 80 mg, about 85 mg, about 90 mg, about 100 mg, about 110 mg, about 120 mg, about 130 mg, about 140 mg, or about 150 mg.

The orodispersible solid dosage form, as described herein, has a hardness that can depend on size and shape as well as on composition, among other characteristics. Tablet hardness can be measured by any method known in the art, for example by a tablet hardness meter (e.g., Schleuniger).

In an embodiment, an about 70 mg to about 80 mg orodispersible solid dosage form has a hardness, at about 25° C. and 60% relative humidity (RH) and/or 30° C. and 65% relative humidity (RH), of about 2 kP to about 7 kP, or about 2 kP to about 6 kP, or about 2 kP to about 5 kP, or about 3 kP to about 7 kP, or about 3 kP to about 6 kP, or about 3 kP to about 5 kP, or about 4.1 kP to about 6.5 kP, or about 4.2 kP to about 5.8 kP, or about 4.2 kP to about 5.3 kP. In an embodiment, the about 70 mg to about 80 mg orodispersible solid dosage form has a hardness of about 2 kP or more, or about 2.3 kP or more, or 2.5 kP or more, or about 2.8 kP or more, or about 3.0 kP or more, or about 3.1 or more, or about 3.2 or more, or about 3.3 or more, or about 3.4 or more, or about 3.5 kP or more, or about 3.6 or more, or about 3.7 or more, or about 3.8 or more, or about 3.9 or more, or about 4 kP or more, or about 4.1 kP or more, or about 4.2 kP or more, or about 4.3 kP or more, or about 4.4 kP or more, or about 4.5 kP or more, or about 4.6 kP or more, or about 4.7 kP or more, or about 4.8 kP or more, or about 4.9 kP or more, or about 5 kP or more, or about 5.1 kP or more, or about 5.2 kP or more, or about 5.3 kP or more, or about 5.5 kP or more, or about 5.8 kP or more, or about 6.0 kP or more, or about 6.2 kP or more, or about 6.5 kP or more, or about 6.8 kP or more, up to about 7 kP. Such hardness may be referred to as hardness measured at time of manufacture.

In an embodiment, the orodispersible solid dosage form has a friability value fulfilling requirements of the United States Pharmacopoeia (USP) 1216 for tablet friability tested at 4 minutes, 100 drops at 25 rpm rotation, available at https://www.usp.org/sites/default/files/usp/document/harmonization/gen-chapter/g06_pf_ira_32_2_2006.pdf, which is incorporated by reference herein. In some embodiments, an orodispersible solid dosage form has a friability of 0.4% or less, or 0.3% or less, or 0.2% or less, or 0.1% or less.

In an embodiment, the orodispersible solid dosage form is stable (stable orodispersible solid dosage form) such that at least 90% of the label of the active ingredient(s) are present at 25° C. and 60% relative humidity (RH), 30° C. and 65% relative humidity (RH), and/or 40° C. and 75% relative humidity (RH) for at least one month, or at least two months, or at least three months, or at least four months, or at least five months, or at least six months, or at least seven months, or at least eight months, or at least nine months, or at least ten months, or at least eleven months, or at least twelve months after being tested according to high-performance liquid chromatography. In accordance with this stability assay, the excitation wavelength of 210 nm and an emission wavelength of 310 nm are used for the quantification of ethinyl estradiol, and a wavelength from 200 nm to 400 nm with a diode-array detector (DAD) is used to identify the norethindrone acetate and ethinyl estradiol.

In an embodiment, the uniformity of the orodispersible solid dosage form is determined by several different assessments, including but not limited to, a powder mix uniformity or blend uniformity assessment, a stratified content uniformity assessment (i.e., an in process dosage unit assessment), and/or a content uniformity assessment (i.e., assessment of the final dosage form).

The blend uniformity assessment and the stratified content uniformity assessment are performed as per recommendations by the International Society of Pharmaceutical Engineering (ISPE) as detailed in "Recommendations for the Assessment of Blend and Content Uniformity: Modifications to Withdrawn FDA Draft Stratified Sampling Guidance" (Journal of Pharmaceutical Innovation (2015) 10: 76-83) and "Assessment of Blend and Content Uniformity. Technical Discussion of Sampling Plans and Application of ASTM E2709/E2810 (Journal of Pharmaceutical Innovation (2015) 10: 84-97). Both the blend uniformity assessment and the stratified content uniformity assessment are performed in two stages, with stage 2 assessments only performed in the event of failing to meet the stage 1 acceptance criteria. Specifically, the acceptance criteria for the blend uniformity assessment at stage 1 is when the relative standard derivation (RSD) is ≤3.0%. If it is necessary to proceed to stage 2, the acceptance criteria for the blend uniformity assessment at stage 2 is when the relative standard derivation (RSD) is ≤5.0%. If at stage 2, the blend uniformity has relative standard derivation of >3.0% and ≤5.0%, then the stratified content uniformity assessment is conducted, and proceeds directly to stage 2. The blend is considered uniform and processed into tablets if the blend has a relative standard derivation (RSD) is ≤3.0% (stage 1) or ≤5.0% (Stage 2).

For the stratified content uniformity assessment, forty (40) locations are assessed through the compression run. Acceptance criteria is based on label claim limits for individual tablets. Specifically, at stage 1, the acceptance criteria is based on testing three (3) dosage units from 20 pre-determined locations from across compression, and all individual values must fall within 75.0-125.0% label, and the dosage forms must satisfy ASTM E2709/E2810 tests to provide appropriate level of assurance to comply with United States Pharmacopoeia (USP) 905 (USP43-NF38-7183). If the acceptance criteria is not met at stage 1, the testing moves to stage 2. At stage 2, the acceptance criteria is based on testing the remaining 20 pre-determined locations, and all individual values must fall within 75.0-125.0% label, and the dosage forms must satisfy ASTM E2709/E2810 tests to provide appropriate level of assurance to comply with USP 905 (USP43-NF38-7183). For each set of results generated, the standard deviation of results (both between and within each location assessed) is determined. Based on the calculated standard deviations, acceptable upper and lower limits for the mean drug content are determined. Tools to assist the statistical analysis are available at https://ispe.org/initiatives/blend-uniformity-content-uniformity/tools. The oral dosage form(s) (e.g., tablet(s)) which satisfy the acceptance criteria described herein for the stratified content uniformity assessment are considered uniform tablets.

The content uniformity assessment is also performed in two stages, with stage 2 assessments only performed in the event of failing to meet the stage 1 acceptance criteria. Specifically, at stage 1, the acceptance criteria is based on testing ten (10) dosage units (out of a total of thirty (30) dosage units) to determine that the acceptance value is ≤15.0 as described United States Pharmacopoeia (USP) 905 (USP43-NF38-7183). If the acceptance criteria are not met at stage 1, the testing moves to stage 2. At stage 2, the acceptance criteria is based on testing the remaining twenty (20) dosage unit, to determine that the acceptance value is ≤15.0, in accordance with the methods and procedures of stage 1. The oral dosage form(s) (e.g., tablet(s)) which satisfy the acceptance criteria described herein for the two-stage content uniformity assessment are considered uniform tablets.

EXAMPLES

Specific embodiments of the invention will now be demonstrated by reference to the following examples. It should be understood that these examples are disclosed solely by way of illustrating the invention and should not be taken in any way to limit the scope of the present invention.

Example 1

An orodispersible solid dosage form in accordance with the invention into which at least one active ingredient can be incorporated is presented below in the following tables.

TABLE 1

| Intragranular Component | |
| --- | --- |
| | % w/w |
| Diluent (microcrystalline cellulose and mannitol) | 91.77 |
| Disintegrant (croscarmellose sodium) | 2.69 |
| Binder (pregelatinized starch) | 5.37 |
| Additional Agents | 0.17 |
| Total | 100.00 |

TABLE 2

| Extragranular Component | |
| --- | --- |
| | % w/w |
| Diluent (microcrystalline cellulose and mannitol) | 79.89 |
| Disintegrant (croscarmellose sodium) | 7.01 |
| Binder (pregelatinized starch) | 4.68 |
| Additional Agents | 8.42 |
| Total | 100.00 |

To prepare the orodispersible solid dosage form, a granulating solution was formulated. The granulating solution may contain a first active ingredient, and optionally a second active ingredient, in at least one solvent. The intragranular component, as shown above in Table 1, was granulated with the granulating solution. The granulated mixture was then blended with the extragranular component, as shown above in Table 2. Finally, the blended ingredients were compressed into an orodispersible solid dosage form. The intragranular component was about 47% w/w of the orodispersible solid dosage form. The final orodispersible solid dosage form of Example 1 was a 80 mg tablet with a composition as presented below in Table 3.

TABLE 3

| Final Tablet | |
| --- | --- |
| | % w/w |
| Diluent (microcrystalline cellulose and mannitol) | 85.42 |
| Disintegrant (croscarmellose sodium) | 5.00 |
| Binder (pregelatinized starch) | 5.00 |
| Additional Agents | 4.58 |
| Total | 100.00 |

This 80 mg tablet had a hardness of 5.1 kP with a compression force of 5.1 kN, a friability at 4 minutes of 0% a friability at 16 minutes of 0.2% and a disintegration time of 21 seconds, as shown in FIG. 1. Testing was performed based on methods described herein, including USP 701 and 1216, as mentioned above.

Example 2

An orodispersible solid dosage form in accordance with the invention into which at least one active ingredient can be incorporated is presented below in the following tables.

TABLE 4

| Intragranular Component | |
| --- | --- |
| | % w/w |
| Diluent (microcrystalline cellulose and mannitol) | 94.77 |
| Disintegrant (croscarmellose sodium) | 2.81 |
| Binder (povidone) | 2.25 |
| Additional Agents | 0.18 |
| Total | 100.00 |

TABLE 5

| Extragranular Component | |
| --- | --- |
| | % w/w |
| Diluent (microcrystalline cellulose and mannitol) | 76.11 |
| Disintegrant (croscarmellose sodium) | 6.76 |
| Binder (pregelatinized starch) | 9.02 |
| Additional Agents | 8.11 |
| Total | 100.00 |

To prepare the orodispersible solid dosage form, a granulating solution was formulated. The granulating solution may contain a first active ingredient, and optionally a second active ingredient, in at least one solvent. The intragranular component, as shown above in Table 4, was granulated with the granulating solution. The granulated mixture was then blended with the extragranular component, as shown above in Table 5. Finally, the blended ingredients were compressed into an orodispersible solid dosage form. In this example, the intragranular component was about 45% w/w of the orodispersible solid dosage form. The final orodispersible solid dosage form of Example 2 was a 80 mg tablet with a composition as presented below in Table 6.

TABLE 6

| Final Tablet | |
|---|---|
| | % w/w |
| Diluent (microcrystalline cellulose and mannitol) | 84.42 |
| Disintegrant (croscarmellose sodium) | 5.00 |
| Binder (povidone and pregelatinized starch) | 6.00 |
| Additional Agents | 4.58 |
| Total | 100.00 |

Figure 2:
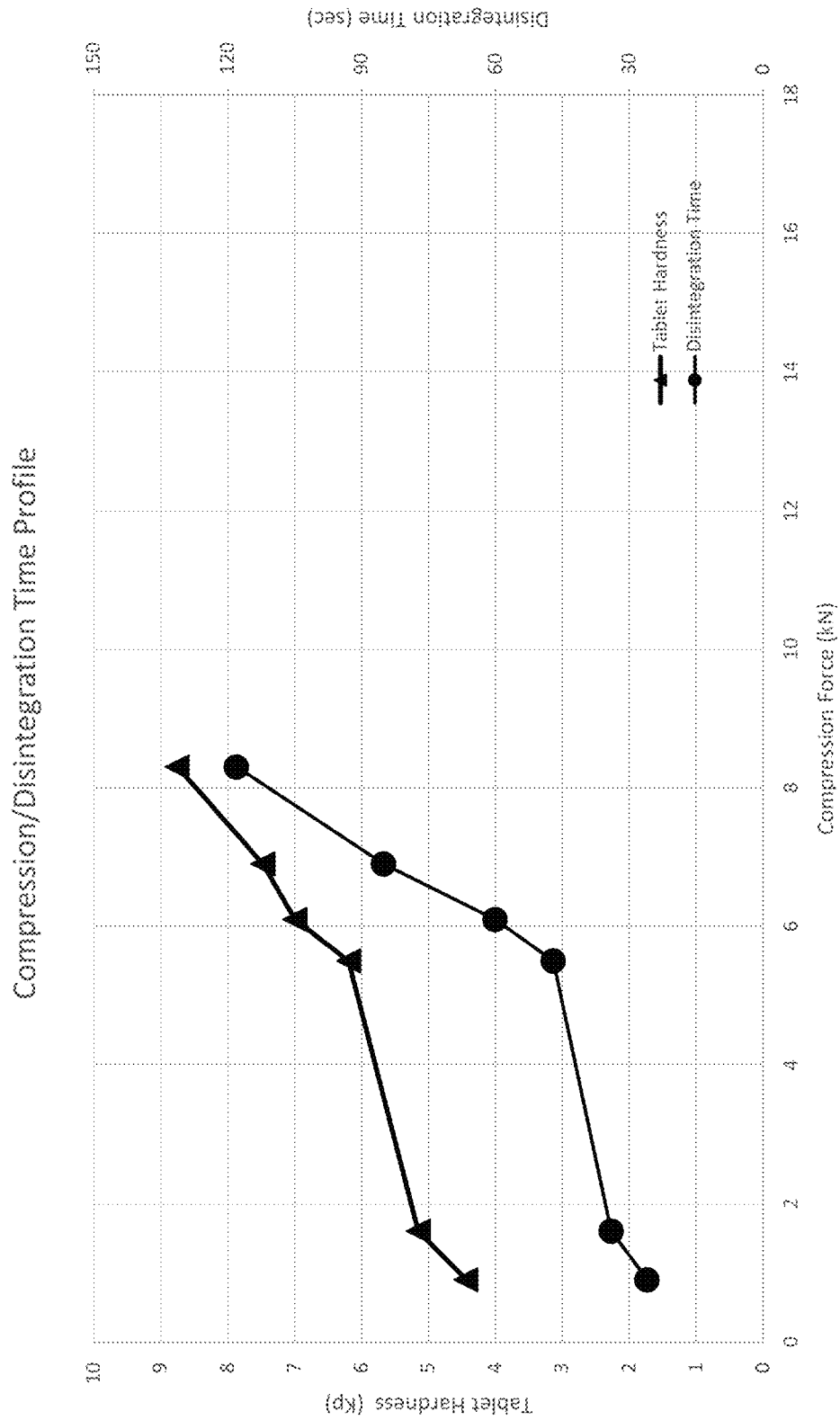
FIG. 2 is a graph depicting the compression force, hardness and disintegration time of an orodispersible solid dosage form of Example 2.

This 80 mg tablet had a hardness of 4.2 kP with a compression force of 1.4 kN, a friability at 4 minutes of 0.1% a friability at 16 minutes of 0.3% and a disintegration time of 28 seconds, as shown in FIG. 2. Testing was performed based on methods described herein, including USP 701 and 1216, as mentioned above.

Example 3

An orodispersible solid dosage form in accordance with the invention into which at least one active ingredient can be incorporated is presented below in the following tables.

TABLE 7

| Intragranular Component | |
|---|---|
| | % w/w |
| Diluent (microcrystalline cellulose and mannitol) | 90.20 |
| Disintegrant (sodium starch glycolate) | 2.58 |
| Binder (pregelatinized starch) | 5.16 |
| Additional Agents | 2.06 |
| Total | 100.00 |

TABLE 8

| Extragranular Component | |
|---|---|
| | % w/w |
| Diluent (microcrystalline cellulose and mannitol) | 85.22 |
| Disintegrant (sodium starch glycolate) | 7.15 |
| Binder (pregelatinized starch) | 4.77 |
| Additional Agents | 2.86 |
| Total | 100.00 |

To prepare the orodispersible solid dosage form, a granulating solution was formulated. The granulating solution may contain a first active ingredient, and optionally a second active ingredient, in at least one solvent. The intragranular component, as shown above in Table 7, was granulated with the granulating solution. The granulated mixture was then blended with the extragranular component, as shown above in Table 8. Finally, the blended ingredients were compressed into an orodispersible solid dosage form. In this example, the intragranular component was about 48% w/w of the orodispersible solid dosage form. The final orodispersible solid dosage form of Example 3 was a 80 mg tablet with a composition as presented below in Table 9.

TABLE 9

| Final Tablet | |
|---|---|
| | % w/w |
| Diluent (microcrystalline cellulose and mannitol) | 87.61 |
| Disintegrant (sodium starch glycolate) | 4.96 |
| Binder (pregelatinized starch) | 4.96 |
| Additional Agents | 2.48 |
| Total | 100.00 |

Figure 3:
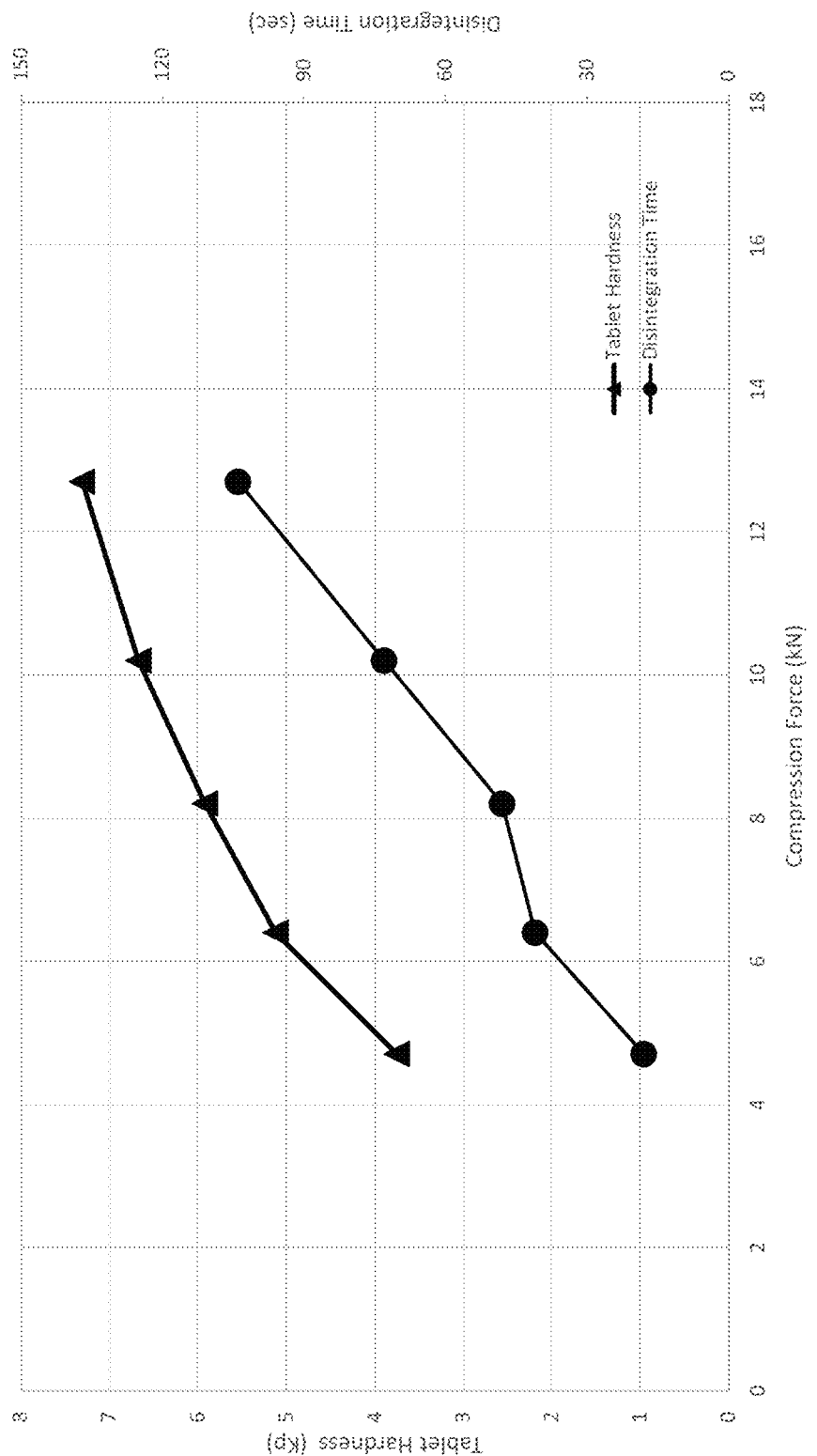
FIG. 3 is a graph depicting the compression force, hardness and disintegration time of an orodispersible solid dosage form of Example 3.

This 80 mg tablet had a hardness of 4.7 kP with a compression force of 5.8 kN, a friability at 4 minutes of 0.1% a friability at 16 minutes of 0.2% and a disintegration time of 28 seconds, as shown in FIG. 3. Testing was performed based methods described herein, including USP 701 and 1216, as mentioned above.

Example 4

An orodispersible solid dosage form in accordance with the invention into which at least one active ingredient can be incorporated is presented below in the following tables.

TABLE 10

| Intragranular Component | |
|---|---|
| | % w/w |
| Diluent (microcrystalline cellulose and mannitol) | 90.04 |
| Disintegrant (croscarmellose sodium) | 3.43 |
| Binder (pregelatinized starch) | 5.15 |
| Additional Agents | 1.37 |
| Total | 100.00 |

TABLE 11

| Extragranular Component | |
|---|---|
| | % w/w |
| Diluent (microcrystalline cellulose and mannitol) | 81.32 |
| Disintegrant (croscarmellose sodium) | 8.90 |
| Binder (pregelatinized starch) | 4.45 |
| Additional Agents | 5.34 |
| Total | 100.00 |

To prepare the orodispersible solid dosage form, a granulating solution was formulated. The granulating solution may contain a first active ingredient, and optionally a second active ingredient, in at least one solvent. The intragranular component, as shown above in Table 10, was granulated with the granulating solution. The granulated mixture was then blended with the extragranular component, as shown above in Table 11. Finally, the blended ingredients were compressed into an orodispersible solid dosage form. In this example, the intragranular component was about 72% w/w of the orodispersible solid dosage form. The final orodispersible solid dosage form of Example 4 was a 80 mg tablet with a composition as presented below in Table 12.

TABLE 12

Final Tablet

| | % w/w |
|---|---|
| Diluent (microcrystalline cellulose and mannitol) | 87.61 |
| Disintegrant (croscarmellose sodium) | 4.96 |
| Binder (pregelatinized starch) | 4.96 |
| Additional Agents | 2.48 |
| Total | 100.00 |

Figure 4:
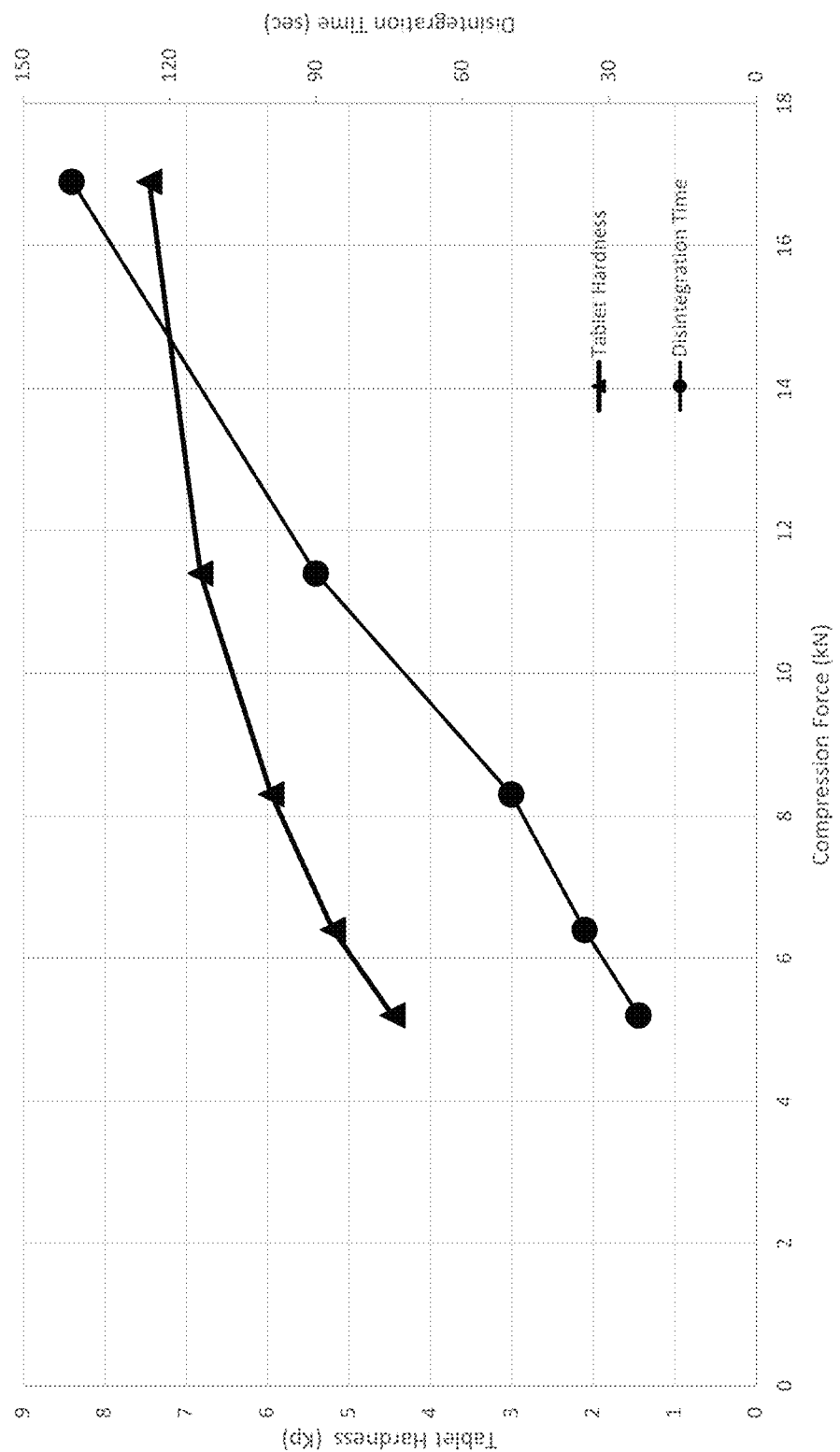
FIG. 4 is a graph depicting the compression force, hardness and disintegration time of an orodispersible solid dosage form of Example 4.

This 80 mg tablet had a hardness of 4.6 kP with a compression force of 5.2 kN, a friability at 4 minutes of 0.1% a friability at 16 minutes of 0.1% and a disintegration time of 21 seconds, as shown in FIG. 4. Testing was performed based methods described herein, including USP 701 and 1216, as mentioned above.

Example 5

An orodispersible solid dosage form in accordance with the invention into which at least one active ingredient can be incorporated is presented below in the following tables.

TABLE 13

Intragranular Component

| | % w/w |
|---|---|
| Diluent (microcrystalline cellulose and mannitol) | 94.05 |
| Disintegrant (croscarmellose sodium) | 2.71 |
| Binder (povidone) | 1.08 |
| Additional Agents | 2.16 |
| Total | 100.00 |

TABLE 14

Extragranular Component

| | % w/w |
|---|---|
| Diluent (microcrystalline cellulose and mannitol) | 81.26 |
| Disintegrant (croscarmellose sodium) | 6.86 |
| Binder (pregelatinized starch) | 9.14 |
| Additional Agents | 2.74 |
| Total | 100.00 |

To prepare the orodispersible solid dosage form, a granulating solution was formulated. The granulating solution may contain a first active ingredient, and optionally a second active ingredient, in at least one solvent. The intragranular component, as shown above in Table 13, was granulated with the granulating solution. The granulated mixture was then blended with the extragranular component, as shown above in Table 14. Finally, the blended ingredients were compressed into an orodispersible solid dosage form. In this example, the intragranular component was about 46% w/w of the orodispersible solid dosage form. The final orodispersible solid dosage form of Example 5 was a 80 mg tablet with a composition as presented below in Table 15.

TABLE 15

Final Tablet

| | % w/w |
|---|---|
| Diluent (microcrystalline cellulose and mannitol) | 87.12 |
| Disintegrant (croscarmellose sodium) | 4.96 |
| Binder (povidone and pregelatinized starch) | 5.45 |
| Additional Agents | 2.48 |
| Total | 100.00 |

Figure 5:
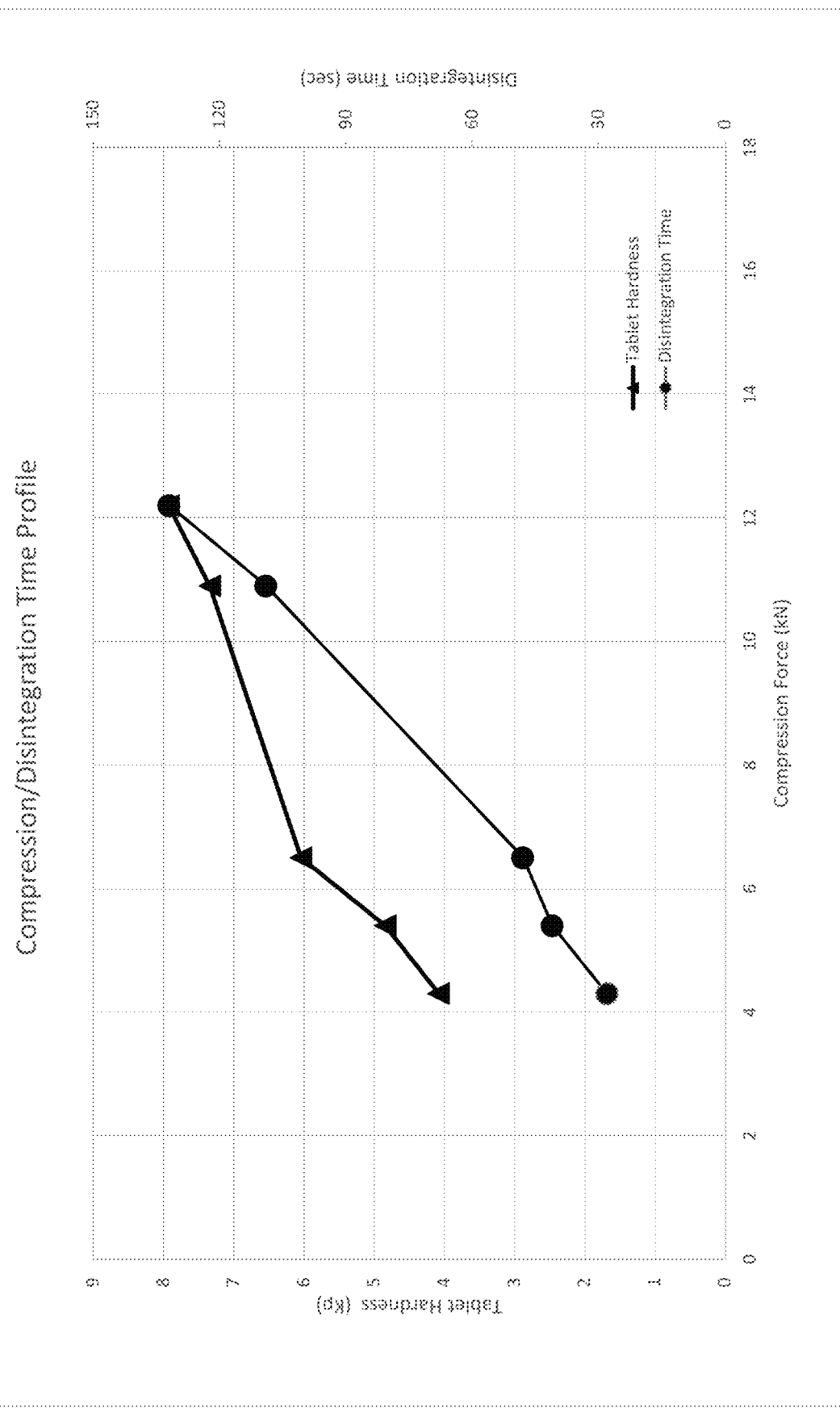
FIG. 5 is a graph depicting the compression force, hardness and disintegration time of an orodispersible solid dosage form of Example 5.
Figure 6:
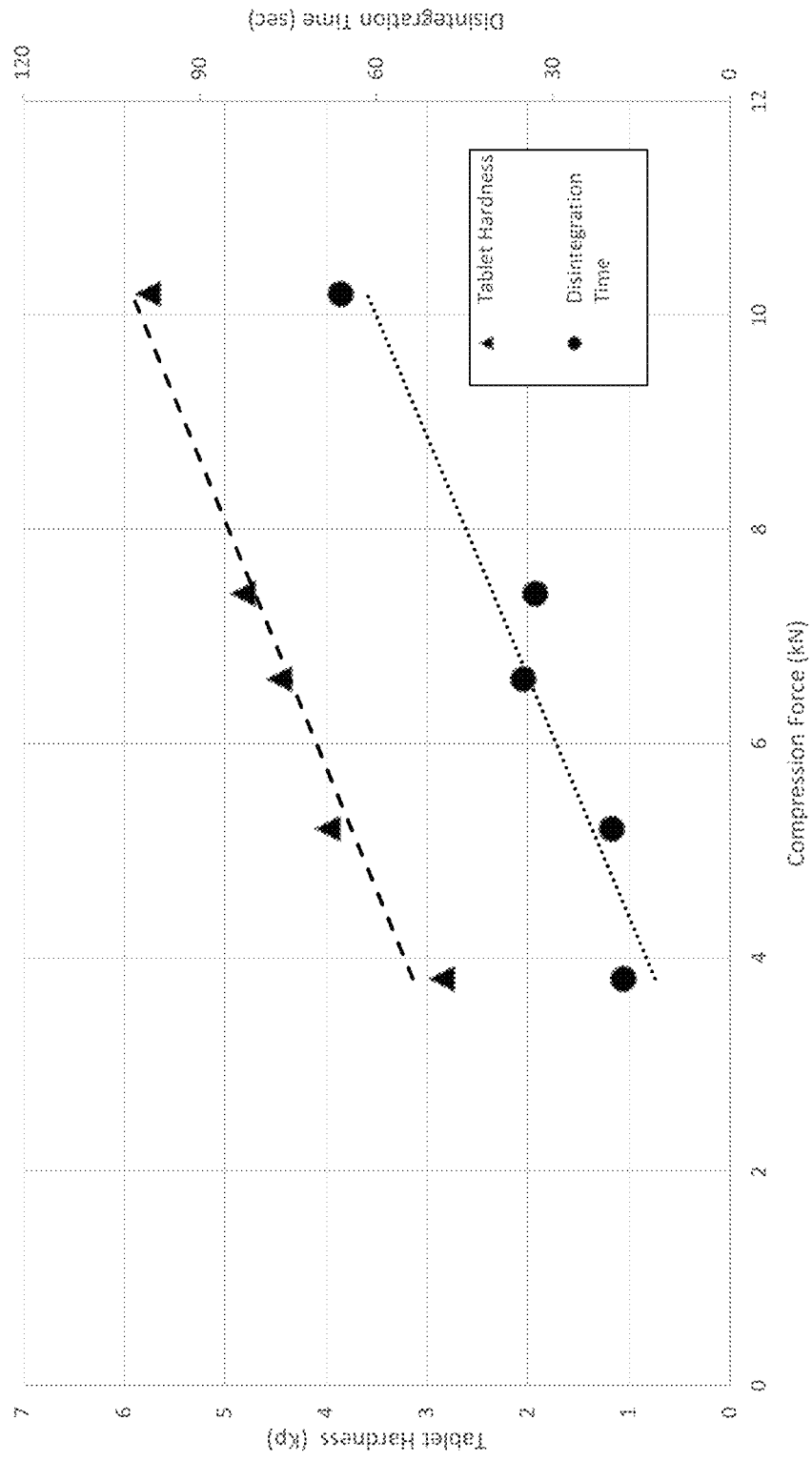
FIG. 6 is a graph depicting the compression force, hardness and disintegration time of an orodispersible solid dosage form of Example 6.
Figure 7:
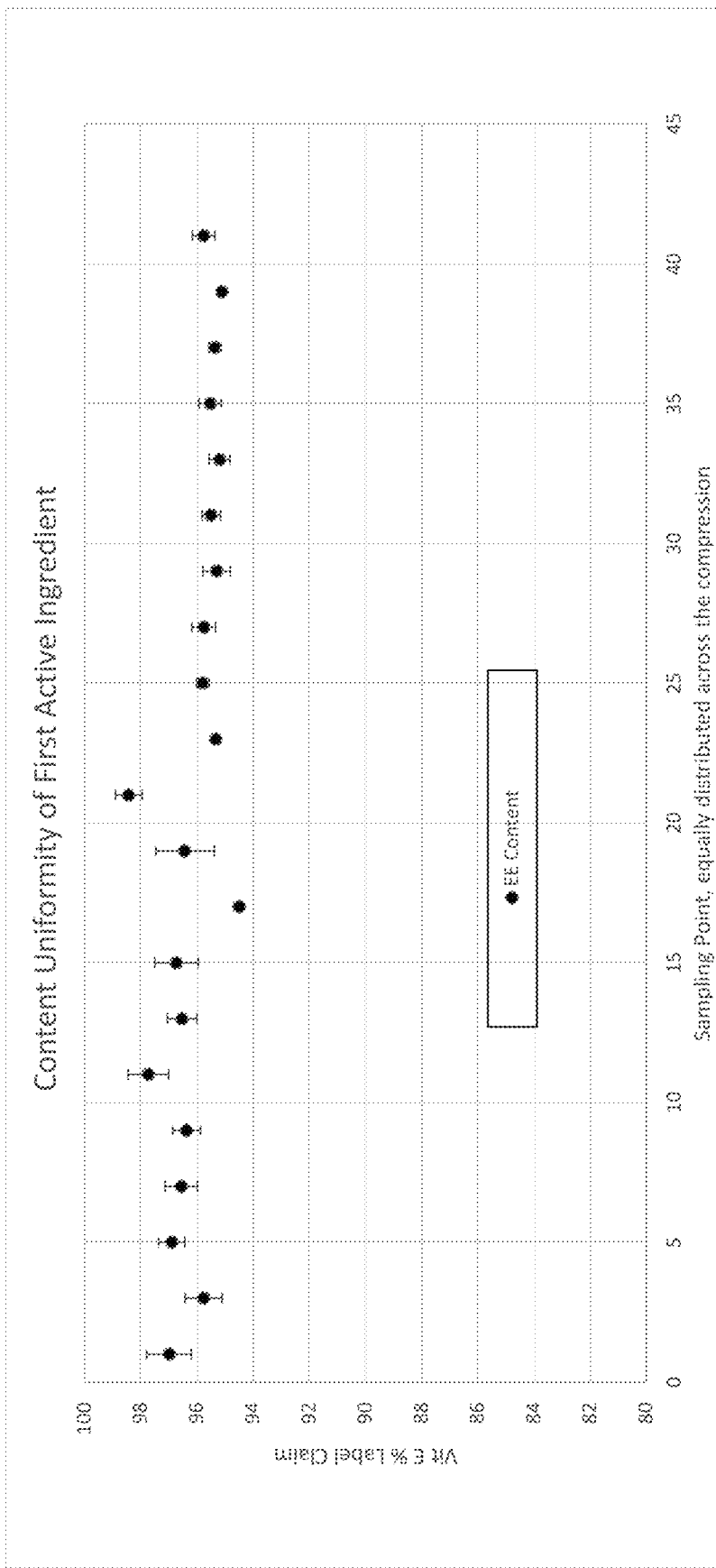
FIG. 7 is a graph depicting the content uniformity of the first active ingredient of Example 6, i.e., ethinyl estradiol.
Figure 8:
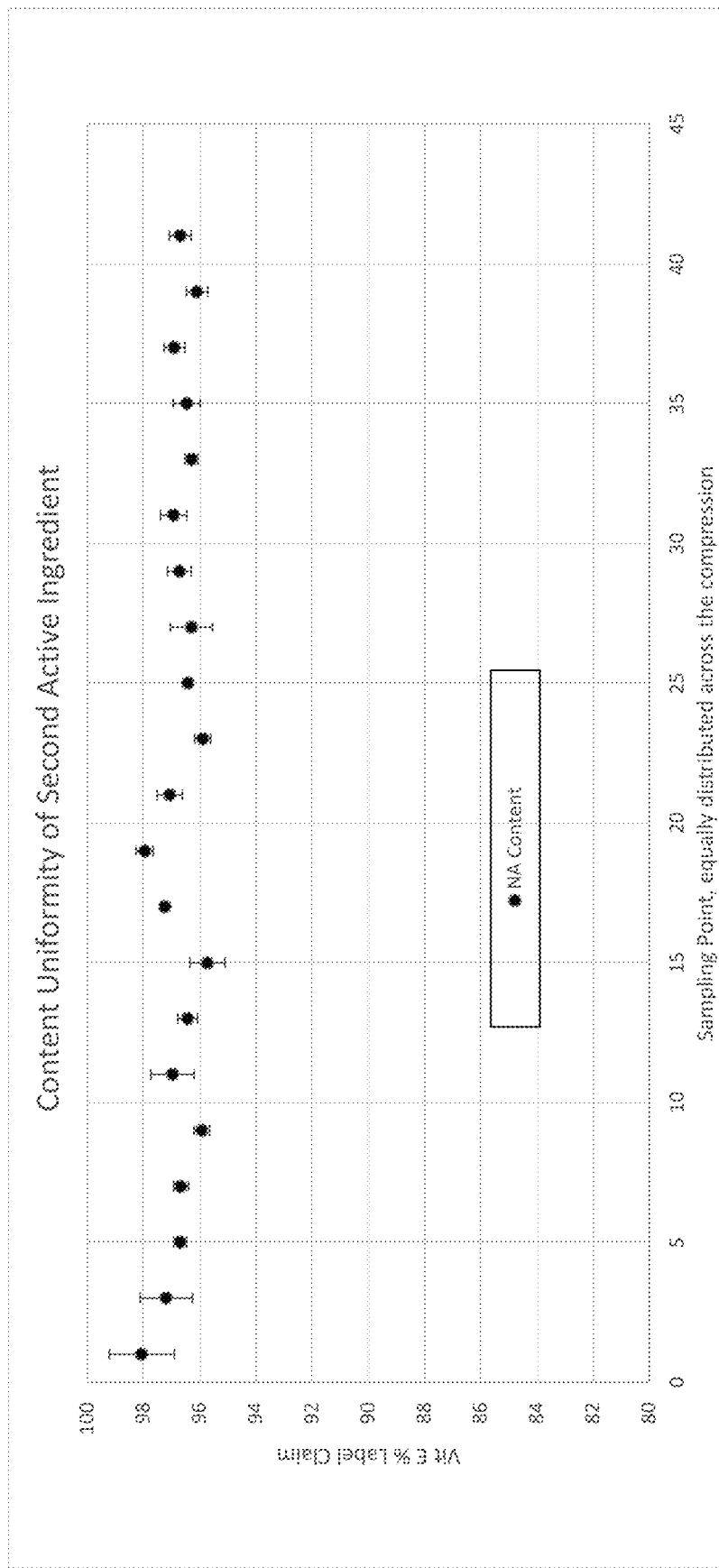
FIG. 8 is a graph depicting the content uniformity of the second active ingredient of Example 6, i.e., norethindrone acetate.

This 80 mg tablet had a hardness of 4 kP with a compression force of 4.4 kN, a friability at 4 minutes of 0.1% a friability at 16 minutes of 0.2% and a disintegration time of 26 seconds, as shown in FIG. 5. Testing was performed based methods described herein, including USP 701 and 1216, as mentioned above.

Example 6

An orodispersible solid dosage form in accordance with the invention is presented below in Tables 16-18.

TABLE 16

Final Tablet

| | % w/w |
|---|---|
| $1^{st}$ Active Ingredient (Ethinyl estradiol) | 0.03 |
| $2^{nd}$ Active Ingredient (Norethindrone acetate) | 1.43 |
| Diluent (microcrystalline cellulose and mannitol) | 86.54 |
| Disintegrant (croscarmellose sodium) | 5.0 |
| Binder (pregelatinized starch) | 5.0 |
| Additional Agents | 2.0 |
| Total | 100.00 |

TABLE 17

Intragranular Component

| | % w/w |
|---|---|
| $1^{st}$ Active Ingredient (Ethinyl estradiol) | 0.06 |
| $2^{nd}$ Active Ingredient (Norethindrone acetate) | 2.94 |
| Diluent (microcrystalline cellulose and mannitol) | 89.07 |
| Disintegrant (croscarmellose sodium) | 2.57 |
| Binder (pregelatinized starch) | 5.15 |
| Additional Agents | 0.21 |
| Total | 100.00 |

TABLE 18

Extragranular Component

| | % w/w |
|---|---|
| Diluent (microcrystalline cellulose and mannitol) | 84.15 |
| Disintegrant (croscarmellose sodium) | 7.30 |
| Binder (pregelatinized starch) | 4.86 |
| Additional Agents | 3.69 |
| Total | 100.00 |

To prepare the orodispersible solid dosage, a granulating solution was prepared by dispersing the $1^{st}$ active ingredient (ethinyl estradiol) in a solution of water and ethanol. The granulating solution was granulated with the diluents (microcrystalline cellulose and mannitol), the disintegrant (croscarmellose sodium), the binder (pregelatinized starch) and the 2$^{nd}$ active ingredient (norethindrone acetate) The granulated mixture was then blended with the extragranular diluents (microcrystalline cellulose and mannitol), the extragranular disintegrant (croscarmellose sodium) and the extragranular binder (pregelatinized starch). Finally, the blended ingredients were compressed into an orodispersible solid dosage form. In this example, the intragranular component was about 49% w/w of the orodispersible solid dosage form. The final orodispersible solid dosage form of Example 6 was a 70 mg tablet with a composition as presented in Table 16.

This 70 mg tablet had a hardness of 3.9 kP, a friability at 4 minutes of 0% a friability at 16 minutes of 0.1% and a disintegration time of 24 seconds. A suitable assay test, such as the tests described in USP-NF Ethinyl Estradiol and Norethindrone Acetate Tablets (2020), was used to determine uniformity and the samples readily passed. Testing was performed based methods described herein, including USP 701 and 1216, as mentioned above.

Tablets having the formulation in accordance with Table 16 were produced in batches and stability tests, as described herein, were conducted. Specifically, the formulation was analyzed at 0 months, 1 month, 3 months and 6 months at 25° C. and 60% relative humidity (RH), 30° C. and 65% relative humidity (RH), and 40° C. and 75% relative humidity (RH) for both the active ingredients (ethinyl estradiol and norethindrone acetate) content, total related substance content, dissolution of active ingredients, and disintegration time for the tablet. The results of the evaluations are set forth in Tables 19-27 presented below. As can be seen from the results, even after 6 months, these formulations are stable as the assay values did not change in a meaningful manner and the active ingredients were present at over 90% of the label claim (LC) (see Tables 19 and 21) with minimal amounts of related substances (see Tables 20 and 22). Tables 23-27 demonstrate that the disintegration and dissolution also remain consistent.

TABLE 19

Stability of ethinyl estradiol

| Timepoint | Limit | EE (25° C./ 60% RH) | EE (30° C./ 65% RH) | EE (40° C./ 75% RH) |
|---|---|---|---|---|
| 0 | 90% LC | 97.2% | 97.2% | 97.2% |
| 1 | 90% LC | 97.4% | 96.9% | 95.6% |
| 3 | 90% LC | 98.9% | 98.3% | 96.0% |
| 6 | 90% LC | 97.5% o | 95.30% | 92.1% |

TABLE 20

Total Related Substance (including 6-alpha-hydroxy-ethinyl estradiol, 6-beta-hydroxy-ethinyl estradiol, 6-keto-hydroxy-ethinyl estradiol, and any unknown impurities)

| Timepoint | Limit | EE - 25° C./ 60% RH | EE - 30° C./ 65% RH | EE - 40° C./ 75% RH |
|---|---|---|---|---|
| 0 | 5% LC | 0.00% | 0.00% | 0.00% |
| 1 | 5% LC | 0.12% | 0.00% | 0.39% |
| 3 | 5% LC | 0.32% | 0.98% | 1.85% |
| 6 | 5% LC | 0.81% | 1.26% | 3.59 |

TABLE 21

Stability of norethindrone acetate

| Timepoint | Limit | NA (25° C./ 60% RH) | NA (30° C./ 65% RH) | NA (40° C./ 75% RH) |
|---|---|---|---|---|
| 0 | 90% LC | 96.9% | 96.9% | 96.9% |
| 1 | 90% LC | 95.8% | 95.7% | 95.4% |
| 3 | 90% LC | 95.9% | 96% | 94.7% |
| 6 | 90% LC | 95.2% | 93.8% | 92.5% |

TABLE 22

Total Related Substance (including 6-alpha-hydroxy-norethindrone acetate, 6-beta-hydroxy-norethindrone acetate, 6-keto-hydroxy-norethindrone acetate, and any unknown impurities)

| Timepoint | Limit | NA - 25° C./ 60% RH | NA - 30° C./ 65% RH | NA - 40° C./ 75% RH |
|---|---|---|---|---|
| 0 | 5% LC | 0.00% | 0.00% | 0.00% |
| 1 | 5% LC | 0.00% | 0.00% | 0.15% |
| 3 | 5% LC | 0.00% | 0.14% | 0.44% |
| 6 | 5% LC | 0.13% | 0.21% | 1.40% |

TABLE 23

Tablet Disintegration (USP 701)

| Timepoint | Limit | 25° C./ 60% RH | 30° C./ 65% RH | 40° C./ 75% RH |
|---|---|---|---|---|
| 0 | 30 sec | 24 sec | 24 sec | 24 sec |
| 1 | 30 sec | 21 sec | 21 sec | 20 sec |
| 3 | 30 sec | 18 sec | 19 sec | 21 sec |
| 6 | 30 sec | 19 sec | 20 sec | 23 sec |

TABLE 24

Dissolution of norethindrone acetate (USP 711) (15 minutes)

| Timepoint | Limit | 25° C./ 60% RH | 30° C./ 65% RH | 40° C./ 75% RH |
|---|---|---|---|---|
| 0 | 80% LC | 92% | 92% | 92% |
| 1 | 80% LC | 91% | 91% | 89% |
| 3 | 80% LC | 89% | 91% | 89% |
| 6 | 80% LC | 88% | 89% | 83% |

TABLE 25

Dissolution of norethindrone acetate (USP 711) (30 minutes)

| Timepoint | Limit | 25° C./ 60% RH | 30° C./ 65% RH | 40° C./ 75% RH |
|---|---|---|---|---|
| 0 | 80% LC | 96% | 96% | 96% |
| 1 | 80% LC | 94% | 94% | 95% |
| 3 | 80% LC | 94% | 95% | 95% |
| 6 | 80% LC | 93% | 93% | 91% |

TABLE 26

Dissolution of ethinyl estradiol (USP 711) (15 minutes)

| Timepoint | Limit | 25° C./ 60% RH | 30° C./ 65% RH | 40° C./ 75% RH |
|---|---|---|---|---|
| 0 | 80% LC | 97% | 97% | 97% |
| 1 | 80% LC | 96% | 98% | 97% |
| 3 | 80% LC | 98% | 99% | 96% |
| 6 | 80% LC | 96% | 94% | 92% |

TABLE 27

Dissolution of ethinyl estradiol (USP 711) (30 minutes)

| Timepoint | Limit | 25° C./ 60% RH | 30° C./ 65% RH | 40° C./ 75% RH |
|---|---|---|---|---|
| 0 | 80% LC | 98% | 98% | 98% |
| 1 | 80% LC | 96% | 98% | 98% |
| 3 | 80% LC | 100% | 100% | 96% |
| 6 | 80% LC | 96% | 95% | 93% |

A blend uniformity assessment was performed per the criteria escribed herein. After stage 1 of testing, the batch satisfied the acceptance criteria for both norethindrone acetate and ethinyl estradiol (i.e., the % RSD of norethindrone acetate was 0.33 (% of label) and the % RSD of ethinyl estradiol 0.87 (% of label)).

Figure 9:
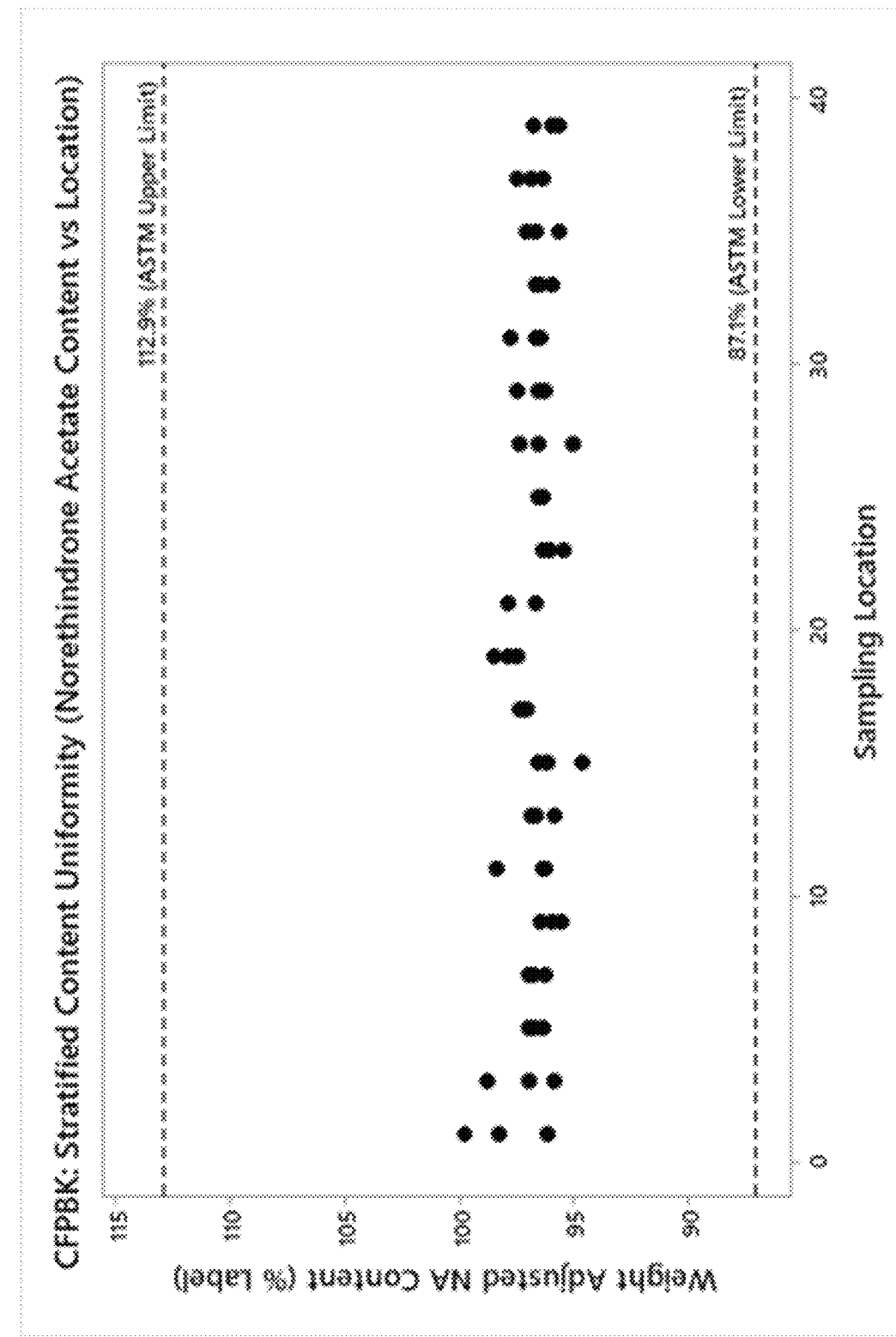
FIG. 9 is a graph depicting the stratified content uniformity of the second active ingredient of Example 6, i.e., norethindrone acetate.
Figure 10:
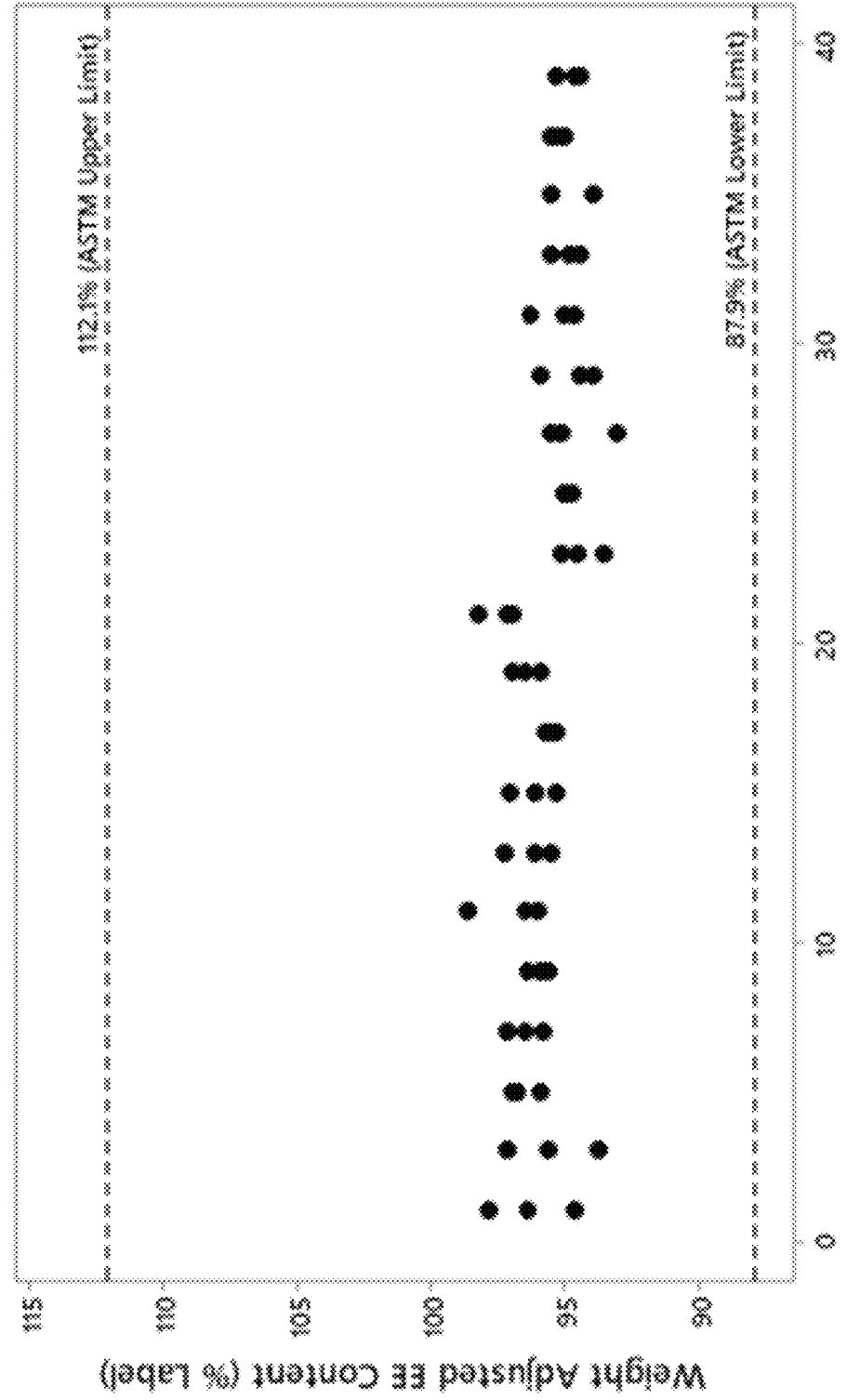
FIG. 10 is a graph depicting the stratified content uniformity of the first active ingredient of Example 6, i.e., ethinyl estradiol.

A stratified content assessment was performed per the criteria described herein. After stage 1, the dosage forms satisfied acceptance criteria for both norethindrone acetate and ethinyl estradiol as shown in FIGS. 9 and 10 (i.e., the values for norethindrone acetate were: mean content 96.7 (% of label), minimum content 94.6 (% of label) and maximum content 99.8 (% of label) and the values for ethinyl estradiol were: mean content 95.7 (% of label), minimum content 97.0 (% of label) and maximum content 98.6 (% of label)).

Figure 11:
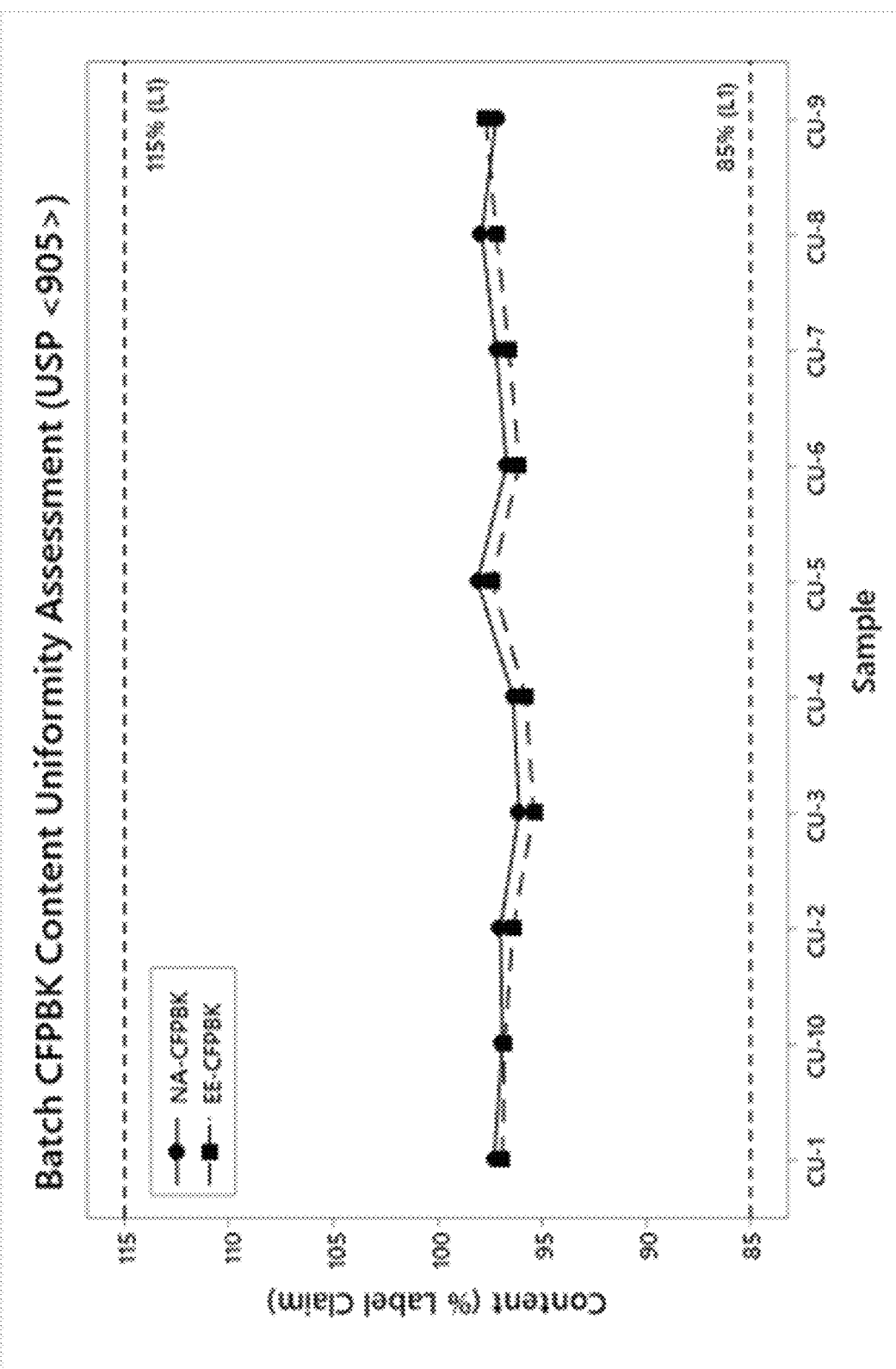
FIG. 11 is a graph depicting the batch content uniformity assessment from Example 6.

A content uniformity assessment was performed per the criteria described herein. After stage 1 of testing, the final dosage forms satisfied the acceptance criteria for both norethindrone acetate and ethinyl estradiol as shown in FIG. 11 (i.e., the acceptance value for norethindrone acetate was 2.9 and the acceptance value for ethinyl estradiol was 3.6).

Example 7

An orodispersible solid dosage form in accordance with the invention is presented below in Tables 28-30.

TABLE 28

Final Tablet

|  | % w/w |
|---|---|
| Ethinyl estradiol | 0.03 |
| Norethindrone acetate | 1.43 |
| Diluent (microcrystalline cellulose and mannitol) | 84.03 |
| Disintegrant (sodium starch glycolate) | 7.5 |
| Binder (pregelatinized starch) | 5.0 |
| Additional Agents | 2.01 |
| Total | 100.00 |

TABLE 29

Intragranular Component

|  | % w/w |
|---|---|
| $1^{st}$ Active Ingredient (Ethinyl estradiol) | 0.06 |
| $2^{nd}$ Active Ingredient (Norethindrone acetate) | 2.98 |
| Diluent (microcrystalline cellulose and mannitol) | 87.60 |
| Disintegrant (sodium starch glycolate) | 3.91 |
| Binder (pregelatinized starch) | 5.21 |
| Additional Agents | 0.24 |
| Total | 100.00 |

TABLE 30

Extragranular Component

|  | % w/w |
|---|---|
| Diluent (microcrystalline cellulose and mannitol) | 80.74 |
| Disintegrant (croscarmellose sodium) | 10.81 |
| Binder (pregelatinized starch) | 4.80 |
| Additional Agents | 3.65 |
| Total | 100.00 |

To prepare the orodispersible solid dosage, a granulating solution was prepared by dispersing the $1^{st}$ active ingredient (ethinyl estradiol) in a solution of water and ethanol. The granulating solution was granulated with the diluents (microcrystalline cellulose and mannitol), the disintegrant (croscarmellose sodium), the binder (pregelatinized starch) and the $2^{nd}$ active ingredient (norethindrone acetate). The granulated mixture was then blended with the extragranular diluents (microcrystalline cellulose and mannitol), the extragranular disintegrant (croscarmellose sodium) and the extragranular binder (pregelatinized starch). Finally, the blended ingredients were compressed into an orodispersible solid dosage form. In this example, the intragranular component was about 48% w/w of the orodispersible solid dosage form. The final orodispersible solid dosage form of Example 7 was a 70 mg tablet with a composition as presented in Table 28.

This 70 mg tablet had a hardness of 2.2 kP, a friability at 4 minutes of 0.1% a friability at 16 minutes of 0.0% and a disintegration time of 19 seconds. A suitable assay method, such as those described in Example 6, was used to determine uniformity and the samples readily passed. Testing was performed based on methods described herein, including USP 701 and 1216, as mentioned above.

Tablets having the formulation in accordance with Table 28 were produced in batches and stability tests, as described herein, were conducted. Specifically, the formulation was analyzed at 0 months, 1 month, and 3 months at 25° C. and 60% relative humidity (RH), 30° C. and 65% relative humidity (RH), and 40° C. and 75% relative humidity (RH) for both the active ingredients (ethinyl estradiol and norethindrone acetate) content, total related substance content, dissolution of active ingredients, and disintegration time for the tablet. The results of the evaluations are set forth in Tables 31-39 as presented below. As can be seen from the results, even after 3 months the assay values to not change in a meaningful manner and the active ingredients are present at over 90% of the label claim (LC) (see Tables 31 and 33). Tables 35-39 demonstrate that the disintegration and dissolution also remain consistent.

TABLE 31

Stability of ethinyl estradiol

| Timepoint | Limit | EE (25° C./60% RH) | EE (30° C./65% RH) | EE (40° C./75% RH) |
|---|---|---|---|---|
| 0 | 90% LC | 98.4% of label | 98.4% of label | 98.4% of label |
| 1 | 90% LC | 98.8% of label | 98.0% of label | 97.0% of label |
| 3 | 90% LC | 99.1% of label | 98.4% of label | 96.5% of label |

TABLE 32

Total Related Substance (including 6-alpha-hydroxy-ethinyl estradiol, 6-beta-hydroxy-ethinyl estradiol, 6-keto-hydroxy-ethinyl estradiol, and any unknown impurities)

| Timepoint | Limit | EE - 25° C./60% RH | EE - 30° C./65% RH | EE - 40° C./75% RH |
|---|---|---|---|---|
| 0 | 5% LC | <0.1% of label | <0.1% of label | <0.1% of label |
| 1 | 5% LC | 0.0% of label | 0.00% of label | 0.80% of label |
| 3 | 5% LC | 0.0% of label | 0.61% of label | 2.55% of label |

TABLE 33

Stability of norethindrone acetate

| Timepoint | Limit | NA (25° C./60% RH) | NA (30° C./65% RH) | NA (40° C./75% RH) |
|---|---|---|---|---|
| 0 | 90% LC | 100.1% | 100.1% | 100.1% |
| 1 | 90% LC | 96.3% | 95.9% | 95.4% |
| 3 | 90% LC | 97.3% | 96.5% | 95.6% |

TABLE 34

Total Related Substance (including 6-alpha-hydroxy-norethindrone acetate, 6-beta-hydroxy-norethindrone acetate, 6-keto-hydroxy-norethindrone acetate, and any unknown impurities)

| Timepoint | Limit | NA - 25° C./60% RH | NA - 30° C./65% RH | NA - 40° C./75% RH |
|---|---|---|---|---|
| 0 | 5% LC | <0.1% | <0.1% | <0.1% |
| 1 | 5% LC | 0.00% | 0.00% | 0.18% |
| 3 | 5% LC | 0.00% | 0.12% | 0.87% |

TABLE 35

Tablet Disintegration (USP 701)

| Timepoint | Limit | 25° C./60% RH | 30° C./65% RH | 40° C./75% RH |
|---|---|---|---|---|
| 0 | 30 sec | 17 sec | 17 sec | 17 sec |
| 1 | 30 sec | 17 sec | 14 sec | 18 sec |
| 3 | 30 sec | 14 sec | 15 sec | 16 sec |

TABLE 36

Dissolution of norethindrone acetate (USP 711) (15 minutes)

| Timepoint | Limit | 25° C./60% RH | 30° C./65% RH | 40° C./75% RH |
|---|---|---|---|---|
| 0 | 80% LC | 91% | 91% | 91% |
| 1 | 80% LC | 88% | 89% | 88% |
| 3 | 80% LC | 8791% | 90% | 83% |

TABLE 37

Dissolution of norethindrone acetate (USP 711) (30 minutes)

| Timepoint | Limit | 25° C./60% RH | 30° C./65% RH | 40° C./75% RH |
|---|---|---|---|---|
| 0 | 80% LC | 96% | 96% | 96% |
| 1 | 80% LC | 94% | 94% | 94% |
| 3 | 80% LC | 96% | 96% | 90% |

TABLE 38

Dissolution of ethinyl estradiol (USP 711) (15 minutes)

| Timepoint | Limit | 25° C./60% RH | 30° C./65% RH | 40° C./75% RH |
|---|---|---|---|---|
| 0 | 80% LC | 101% | 101% | 101% |
| 1 | 80% LC | 98% | 99% | 97% |
| 3 | 80% LC | 97% | 98% | 93% |

TABLE 39

Dissolution of ethinyl estradiol (USP 711) (30 minutes)

| Timepoint | Limit | 25° C./60% RH | 30° C./65% RH | 40° C./75% RH |
|---|---|---|---|---|
| 0 | 80% LC | 102% | 102% | 102% |
| 1 | 80% LC | 99% | 98% | 98% |
| 3 | 80% LC | 99% | 99% | 95% |

A blend uniformity assessment was performed per the criteria described herein. After stage 1 of testing, the batch satisfied the acceptance criteria for both norethindrone acetate and ethinyl estradiol (i.e., the % RSD of norethindrone acetate was 0.92 (% of label) and the % RSD of ethinyl estradiol 0.92 (% of label)).

Figure 12:
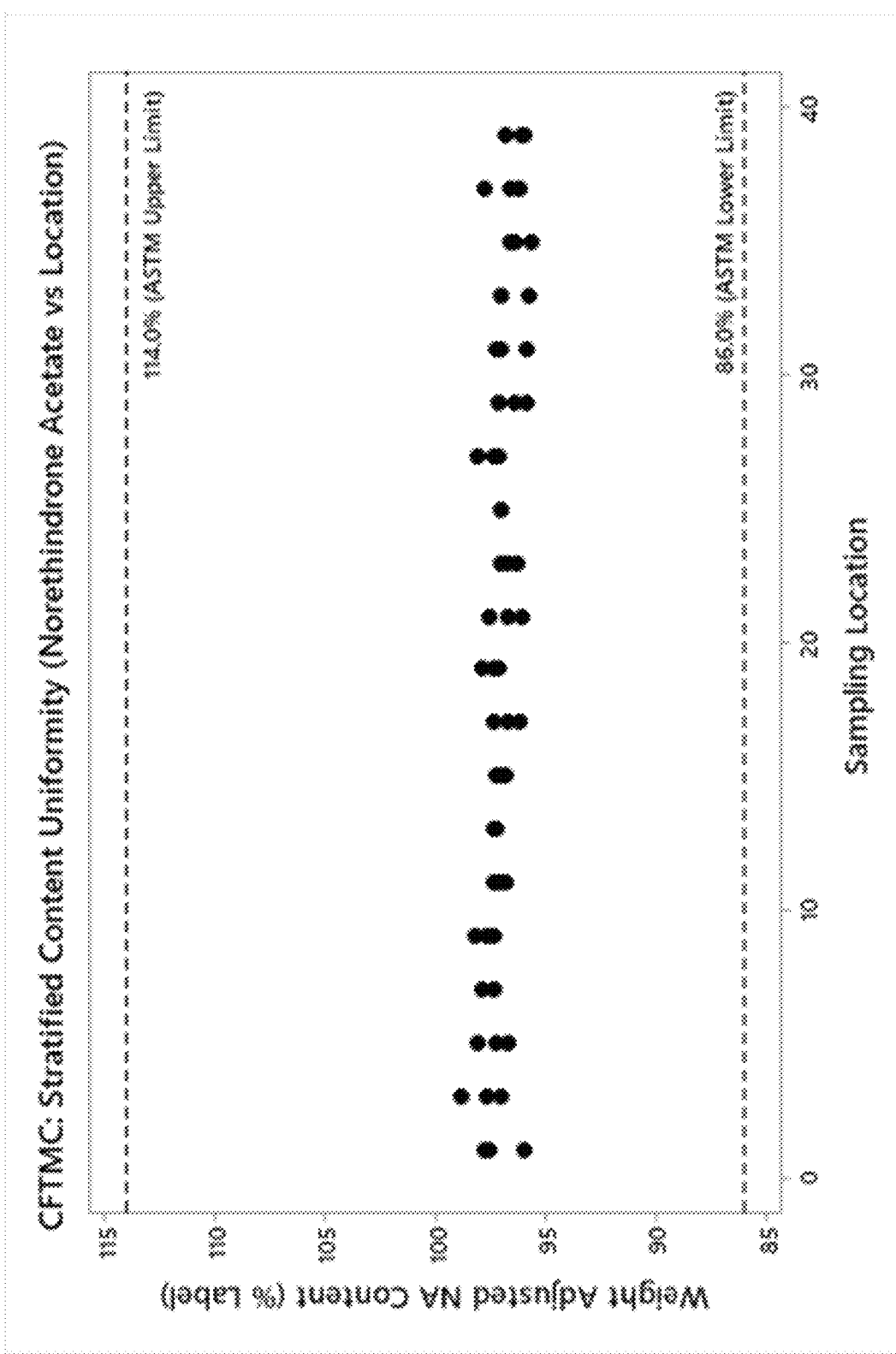
FIG. 12 is a graph depicting the stratified content uniformity of the second active ingredient of Example 7, i.e., norethindrone acetate.
Figure 13:
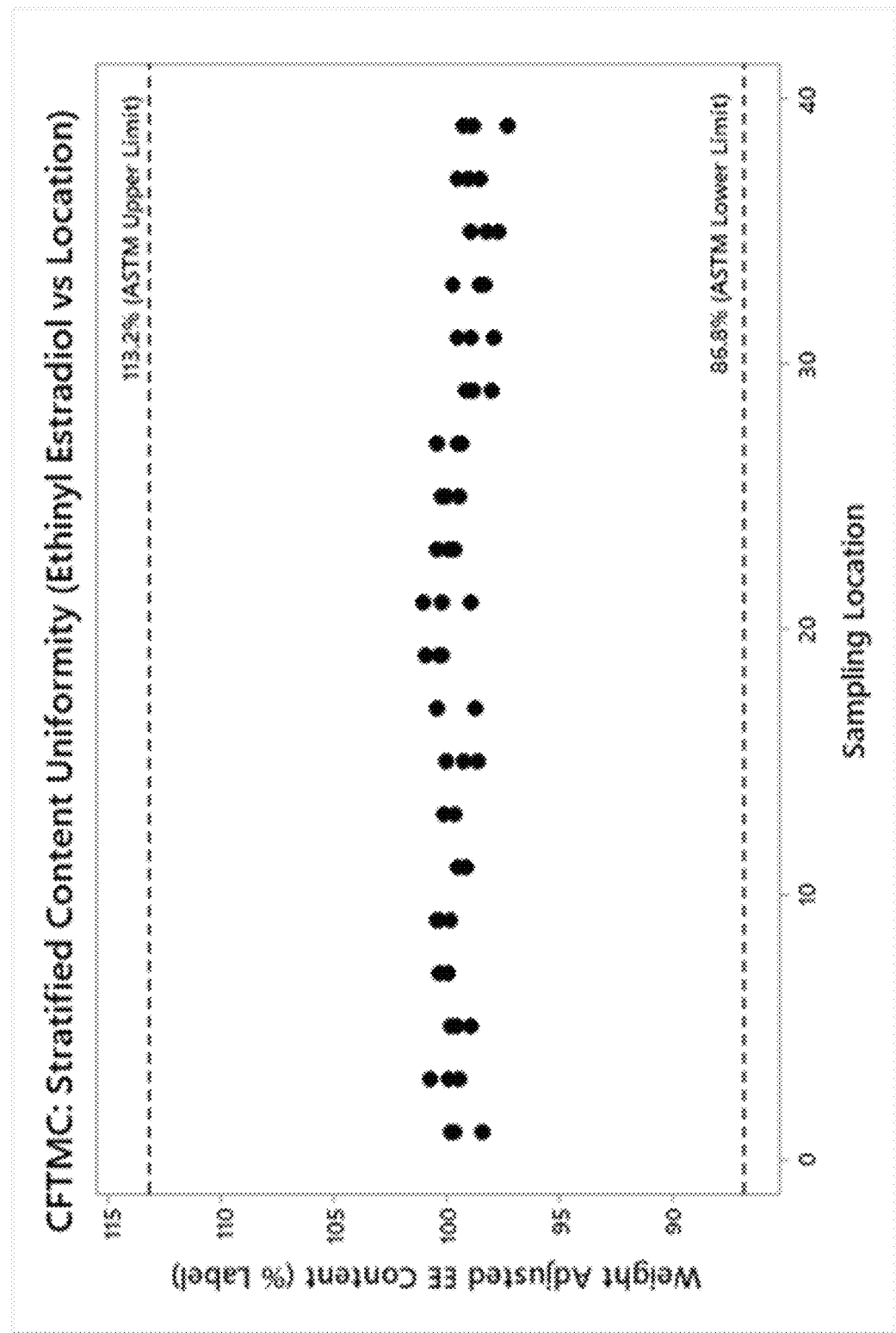
FIG. 13 is a graph depicting the stratified content uniformity of the first active ingredient of Example 7, i.e., ethinyl estradiol.

A stratified content assessment was performed per the criteria described herein. After stage 1, the dosage forms satisfied acceptance criteria for both norethindrone acetate and ethinyl estradiol as shown in FIGS. 12 and 13 (i.e., the values for norethindrone acetate were: mean content 97.0 (% of label), minimum content 95.7 (% of label) and maximum content 98.8 (% of label) and the values for ethinyl estradiol were: mean content 99.5 (% of label), minimum content 97.3 (% of label) and maximum content 101.1 (% of label)).

Figure 14:
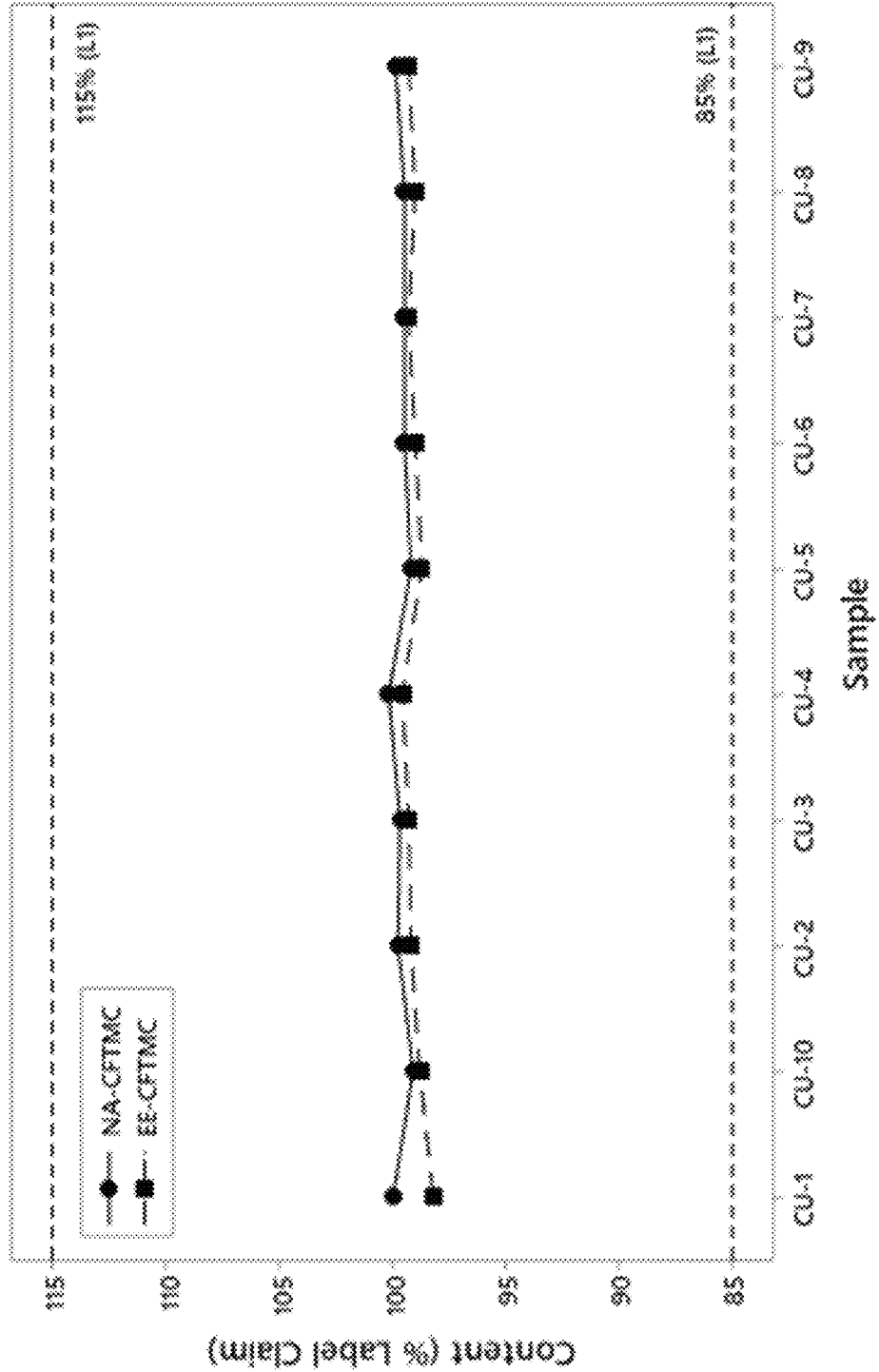
FIG. 14 is a graph depicting the batch content uniformity assessment from Example 7.

A content uniformity assessment was performed per the criteria described herein. After stage 1 of testing, the final dosage forms satisfied the acceptance criteria for both norethindrone acetate and ethinyl estradiol as shown in FIG. 14 (i.e., the acceptance value for norethindrone acetate was 0.8 and the acceptance value for ethinyl estradiol was 1.0).

What is claimed is:

1. An orodispersible solid dosage form consisting of an intragranular component and an extragranular component,
wherein the intragranular component consists of an estrogen, an intragranular diluent, an intragranular binder, an intragranular disintegrant, and, optionally, at least one additional intragranular agent,
wherein the extragranular component consists of an extragranular diluent, an extragranular binder, an extragranular disintegrant, and, optionally, at least one additional extragranular agent,
wherein:
the estrogen is in an amount of up to 0.05% w/w of the orodispersible solid dosage form;

the intragranular diluent is microcrystalline cellulose and mannitol at a content of 84% w/w to 97% w/w of the intragranular component;

the intragranular disintegrant is croscarmellose sodium or sodium starch glycolate at a content of 2.2% w/w to 4.5% w/w of the intragranular component;

the intragranular binder is a pregelatinized starch or povidone at a content of 0.5% w/w to 6% w/w of the intragranular component;

the extragranular diluent is microcrystalline cellulose and mannitol at a content of 72% w/w to 88% w/w of the extragranular component;

the extragranular disintegrant is croscarmellose sodium or sodium starch glycolate at a content of 5% w/w to 12% w/w of the extragranular component;

the extragranular binder is a pregelatinized starch at a content of 3.5% w/w to 12% w/w of the extragranular component;

the at least one additional intragranular agent and the at least one additional extragranular agent are, independently, at least one selected from the group consisting of a progestogen, a lubricant, an antioxidant, a flavoring agent, a sweetener, and a coloring agent, wherein the intragranular component constitutes from 42% w/w to 75% w/w of the orodispersible solid dosage form, wherein the orodispersible solid dosage form disintegrates in 30 seconds or less, wherein the orodispersible solid dosage form has a hardness from 2 kp to 7 kp and a friability of 0.3% or less, and wherein a content uniformity of the estrogen in the orodispersible solid dosage form satisfies ASTM E2709/E2810.

2. The orodispersible solid dosage form of claim 1, wherein the estrogen is selected from the group consisting of ethinyl estradiol, 17β-estradiol, 17β-estradiol-3-acetate, mestranol, conjugated estrogens, estrone, and any salts or combinations thereof.

3. The orodispersible solid dosage form of claim 2, wherein the estrogen is ethinyl estradiol.

4. The orodispersible solid dosage form of claim 1, which contains the progestogen.

5. The orodispersible solid dosage form of claim 4, wherein an amount of the progestogen is 0.40% w/w to 2.2% w/w of the dosage form.

6. The orodispersible solid dosage form of claim 4, wherein the orodispersible solid dosage form contains the progestogen in an amount of 0.3 mg to 1.5 mg.

7. The orodispersible solid dosage form of claim 4, wherein the progestogen is selected from the group consisting of 17-hydroxy progesterone esters and 19-nor-17-hydroxy progesterone esters, 17-alpha-ethinyl testosterone, 17-alpha-ethinyl-19-nortestosterone (norethindrone), norethindrone acetate, norgestrel, nogestamate, desogestrel and D-17-beta-acetoxy-17-beta-ethyl-17-alpha-ethinyl-gon-4-en-3-one oxime, and combinations thereof.

8. The orodispersible solid dosage form of claim 4, wherein the progestogen is norethindrone acetate.

9. The orodispersible solid dosage form of claim 1, wherein the orodispersible solid dosage form is from 60 mg to 90 mg.

10. The orodispersible solid dosage form of claim 1, wherein the orodispersible solid dosage form has a hardness from 2 kp to 6 kp.

11. The orodispersible solid dosage form of claim 1, wherein the intragranular component constitutes 42% w/w to 55% w/w of the orodispersible solid dosage form.

12. The orodispersible solid dosage form of claim 1, wherein the content of croscarmellose sodium or sodium starch glycolate as the intragranular disintegrant is from 2.4% w/w to 4% w/w of the intragranular component.

13. The orodispersible solid dosage form of claim 1, wherein the content of pregelatinized starch as the intragranular binder is from 5% w/w to 6% w/w of the intragranular component.

14. The orodispersible solid dosage form of claim 1, wherein the estrogen is ethinyl estradiol, and wherein the intragranular component further comprises norethindrone acetate.

15. The orodispersible solid dosage form of claim 14, wherein an ethinyl estradiol content is from 0.025% w/w to 0.035% w/w of the orodispersible solid dosage form and a norethindrone acetate content is from 1% w/w to 1.9% w/w of the orodispersible solid dosage form.

16. An orodispersible solid dosage form consisting of an intragranular component and an extragranular component, wherein the intragranular component consists of an estrogen, an intragranular diluent, an intragranular binder, an intragranular disintegrant, and, optionally, at least one additional intragranular agent, wherein the extragranular component consists of an extragranular diluent, an extragranular binder, an extragranular disintegrant, and, optionally, at least one additional extragranular agent, wherein the estrogen is in an amount of up to 0.05% w/w of the orodispersible solid dosage form, wherein the intragranular diluent and the extragranular diluent is microcrystalline cellulose and mannitol, and a total content thereof is from 82% w/w to 89% w/w of the orodispersible solid dosage form, wherein the intragranular binder is pregelatinized starch or povidone and the extragranular binder is pregelatinized starch, and a total content thereof is from 4.5% w/w to 6.5% w/w of the orodispersible solid dosage form, wherein the intragranular disintegrant and the extragranular disintegrant is croscarmellose sodium or sodium starch glycolate, and a total content thereof is from 4.5% w/w to 8% w/w of the orodispersible solid dosage form, wherein the at least one additional intragranular agent and the at least one additional extragranular agent are independently at least one selected from the group consisting of a progestogen, a lubricant, an antioxidant, a flavoring agent, a sweetener, and a coloring agent, wherein the intragranular component constitutes from 42% w/w to 75% w/w of the orodispersible solid dosage form, wherein the orodispersible solid dosage form disintegrates in 30 seconds or less, wherein the orodispersible solid dosage form has a hardness from 2 kp to 7 kp and a friability of 0.3% or less, and wherein a content uniformity of the estrogen in the orodispersible solid dosage form satisfies ASTM E2709/E2810.

17. The orodispersible solid dosage form of claim 16, wherein the estrogen is selected from the group consisting of ethinyl estradiol, 17β-estradiol, 17β-estradiol-3-acetate, mestranol, conjugated estrogens, estrone, and any salts or combinations thereof.

18. The orodispersible solid dosage form of claim 17, wherein the estrogen is ethinyl estradiol.

19. The orodispersible solid dosage form of claim 16, wherein the intragranular component constitutes 42% w/w to 55% w/w of the orodispersible solid dosage form.

20. The orodispersible solid dosage form of claim 19, wherein an ethinyl estradiol content is 0.025% w/w to 0.035% w/w of the orodispersible solid dosage form.

21. The orodispersible solid dosage form of claim 16, which contains norethindrone acetate.

22. The orodispersible solid dosage form of claim 21, wherein a norethindrone acetate content is 1% w/w to 1.9% w/w of the orodispersible solid dosage form.

23. The orodispersible solid dosage form of claim 16, wherein:
the estrogen is in the amount from 0.025% w/w to 0.035% w/w of the orodispersible solid dosage form, and the estrogen is ethinyl estradiol;
a content of microcrystalline cellulose and mannitol in the intragranular component is from 86% w/w to 95% w/w of the intragranular component;
a content of croscarmellose sodium or sodium starch glycolate in the intragranular component is from 2% w/w to 4% w/w of the intragranular component;
a content of pregelatinized starch or povidone in the intragranular component is from 1% w/w to 5.5% w/w of the intragranular component;
a content of microcrystalline cellulose and mannitol in the extragranular component is from 75% w/w to 87% w/w of the extragranular component;
a content of croscarmellose sodium or sodium starch glycolate in the extragranular component is from 6% w/w to 11% w/w of the extragranular component; and
a content of pregelatinized starch in the extragranular component is from 4% w/w to 10% w/w of the extragranular component.

24. The orodispersible solid dosage form of claim 16, wherein:
the estrogen is in the amount from 0.025% w/w to 0.035% w/w of the orodispersible solid dosage form, and the estrogen is ethinyl estradiol;
a content of microcrystalline cellulose and mannitol in the intragranular component is from 87% w/w to 90% w/w of the intragranular component;
a content of croscarmellose sodium or sodium starch glycolate in the intragranular component is from 2.3% w/w to 4% w/w of the intragranular component;
a content of pregelatinized starch in the intragranular component is from 5% w/w to 5.5% w/w of the intragranular component;
a content of microcrystalline cellulose and mannitol in the extragranular component is from 80% w/w to 85% w/w of the extragranular component;
a content of croscarmellose sodium in the extragranular component is from 7% w/w to 11% w/w of the extragranular component; and
a content of pregelatinized starch in the extragranular component is from 4.5% w/w to 5% w/w of the extragranular component.

25. The orodispersible solid dosage form of claim 1, wherein:
the estrogen is in the amount from 0.025% w/w to 0.035% w/w of the orodispersible solid dosage form, and the estrogen is ethinyl estradiol;
the content of microcrystalline cellulose and mannitol in the intragranular component is from 86% w/w to 95% w/w of the intragranular component;
the content of croscarmellose sodium or sodium starch glycolate in the intragranular component is from 2.2% w/w to 4% w/w of the intragranular component;
the content of pregelatinized starch or povidone in the intragranular component is from 1% w/w to 5.5% w/w of the intragranular component;
the content of microcrystalline cellulose and mannitol in the extragranular component is from 75% w/w to 87% w/w of the extragranular component;
the content of croscarmellose sodium or sodium starch glycolate in the extragranular component is from 6% w/w to 11% w/w of the extragranular component; and
the content of pregelatinized starch in the extragranular component content is from 4% w/w to 10% w/w of the extragranular component.

26. The orodispersible solid dosage form of claim 1, wherein:
the estrogen is in the amount from 0.025% w/w to 0.035% w/w of the orodispersible solid dosage form, and the estrogen is ethinyl estradiol;
the content of microcrystalline cellulose and mannitol in the intragranular component is from 87% w/w to 90% w/w of the intragranular component;
the content of croscarmellose sodium or sodium starch glycolate in the intragranular component is from 2.3% w/w to 4% w/w of the intragranular component;
the content of pregelatinized starch in the intragranular component is from 5% w/w to 5.5% w/w of the intragranular component;
the content of microcrystalline cellulose and mannitol in the extragranular component is from 80% w/w to 85% w/w of the extragranular component;
the content of croscarmellose sodium in the extragranular component is from 7% w/w to 11% w/w of the extragranular component; and
the content of pregelatinized starch in the extragranular component is from 4.5% w/w to 5% w/w of the extragranular component.

27. The orodispersible solid dosage form of claim 16, wherein the estrogen is ethinyl estradiol, and wherein the intragranular component contains norethindrone acetate.

28. The orodispersible solid dosage form of claim 1, which is a coated orodispersible tablet.

29. The orodispersible solid dosage form of claim 1, which is an uncoated orodispersible tablet.

30. The orodispersible solid dosage form of claim 16, which is an uncoated orodispersible tablet.

* * * * *